United States Patent
Baram et al.

(10) Patent No.: US 11,123,383 B2
(45) Date of Patent: Sep. 21, 2021

(54) COMPOSITION AND METHODS FOR MICROBIOTA THERAPY

(71) Applicant: MYBIOTICS PHARMA LTD., Ness Ziona (IL)

(72) Inventors: David Baram, Nir-Zvi (IL); David Daboush, Mishmar David (IL); Rachel Diamant, Ein-Vered (IL)

(73) Assignee: MYBIOTICS PHARMA LTD., Ness Ziona (IL)

( * ) Notice: Subject to any disclaimer, the term of this patent is extended or adjusted under 35 U.S.C. 154(b) by 37 days.

(21) Appl. No.: 16/304,297

(22) PCT Filed: May 25, 2017

(86) PCT No.: PCT/IL2017/050587
§ 371 (c)(1),
(2) Date: Nov. 25, 2018

(87) PCT Pub. No.: WO2017/203533
PCT Pub. Date: Nov. 30, 2017

(65) Prior Publication Data
US 2019/0083550 A1    Mar. 21, 2019

Related U.S. Application Data

(60) Provisional application No. 62/341,205, filed on May 25, 2016.

(51) Int. Cl.
| | |
|---|---|
| A61K 35/745 | (2015.01) |
| A61K 35/747 | (2015.01) |
| C12N 1/20 | (2006.01) |
| A61K 35/741 | (2015.01) |
| A61K 35/74 | (2015.01) |
| A61K 35/744 | (2015.01) |
| A61P 1/00 | (2006.01) |

(52) U.S. Cl.
CPC ............ *A61K 35/745* (2013.01); *A61K 35/74* (2013.01); *A61K 35/741* (2013.01); *A61K 35/744* (2013.01); *A61K 35/747* (2013.01); *A61P 1/00* (2018.01); *C12N 1/20* (2013.01)

(58) Field of Classification Search
CPC combination set(s) only.
See application file for complete search history.

(56) References Cited

U.S. PATENT DOCUMENTS

| | | |
|---|---|---|
| 2013/0022575 A1 | 1/2013 | Cassity |
| 2014/0147417 A1 | 5/2014 | Sadowsky et al. |
| 2014/0363398 A1 | 12/2014 | Jones et al. |

FOREIGN PATENT DOCUMENTS

| | | |
|---|---|---|
| DE | 202013103204 U1 | 7/2013 |
| RU | 2580002 C1 | 4/2016 |
| WO | 2004022698 A2 | 3/2004 |
| WO | 2014197562 A1 | 12/2014 |
| WO | 2015134808 A1 | 9/2015 |
| WO | 2016181228 A2 | 11/2016 |

OTHER PUBLICATIONS

Rettedal et al., "Cultivation-based multiplex phenotyping of human gut microbiota allows targeted recovery of previously uncultured bacteria", Nature Communications vol. 5, p. 1-9, (2014).
Zengler et al., "Cultivating the uncultured", Proceedings of the National Academy of Sciences vol. 99, No. 24, 15681-15686, (2002).
Sommer, Morten O "Advancing gut microbiome research using cultivation", Current Opinion in Microbiology, 2015, vol. 27 p. 127-132.
Grossart, et al., "Bacterial Colonization of Particles: Growth and Interactions", Applied and Environmental Microbiology, Jun. 2003, vol. 69, No. 6, p. 3500-3509.
Glushanova N.A., et al., "Bacterial Biofilms in Human Infectious Pathology", Medicine in Kuzbass, 2015, Issue 2, pp. 30-35.

*Primary Examiner* — Heidi Reese
(74) *Attorney, Agent, or Firm* — The Roy Gross Law Firm, LLC; Roy Gross

(57) ABSTRACT

The present invention provides a composition comprising a co-culture of at least two distinct bacterial families, having differing growth and/or proliferative conditions. In some embodiments, the composition comprises a plurality of bacterial genera with high similarity to microbial flora.

15 Claims, 6 Drawing Sheets

COMPOSITION AND METHODS FOR MICROBIOTA THERAPY

CROSS-REFERENCE TO RELATED APPLICATIONS

This application is a National Phase of PCT Patent Application No. PCT/IL2017/050587 having International filing date of May 25, 2017, which claims the benefit of priority of U.S. Patent Application No. 62/341,205 filed on May 25, 2016. The contents of the above applications are all incorporated by reference as if fully set forth herein in their entirety.

FIELD OF INVENTION

This invention, in some embodiments thereof, relates to a composition comprising a plurality of bacterial genera and a method of use thereof such as for treatment of dysbiosis.

BACKGROUND OF THE INVENTION

The gastrointestinal tract harbors an abundant and diverse microbial community. It is a complex system, providing an environment or niche for a community of many different species or organisms, including diverse strains of bacteria. Normal microbial flora also typically inhabits skin, nails, eyes, oral and upper respiratory tract and urogenital tract.

A healthy microbiota requires bacterial colonization which provides the host multiple benefits including resistance to a broad spectrum of pathogens, essential nutrient biosynthesis and absorption, and immune stimulation that maintains a healthy gut epithelium and an appropriately controlled systemic immunity. In settings of 'dysbiosis' or disrupted symbiosis, microbiota functions can be lost or deranged, resulting in increased susceptibility to pathogens, altered metabolic profiles, or induction of proinflammatory signals that can result in local or systemic inflammation or autoimmunity. Thus, microbial flora and specifically the intestinal microbiota, play a significant role in the pathogenesis of many diseases and disorders, including but not limited to, a variety of pathogenic infections of the gut.

There is an ongoing need for compositions and methods for treating or preventing various diseases including chronic disorders as dysbiosis, obesity, infection, colitis, inflammatory bowel disease (such as Crohn's disease), autoimmune diseases and cancer immunotherapy.

SUMMARY OF THE INVENTION

This invention in some embodiments thereof, is related to a composition of a plurality of bacterial genera, wherein said plurality of bacterial genera has high similarity to an origin population of microbiota.

According to one aspect, the present invention provides a synthetic composition comprising a co-culture of at least two distinct bacterial families having differing growth and/or proliferative conditions.

According to another aspect, the present invention provides a synthetic composition comprising a plurality of bacterial genera and a plurality of particles, wherein the plurality of bacterial genera is (i) a co-culture of at least two distinct bacterial families, having differing growth and/or proliferative conditions, and (ii) having at least 30% similarity to a microbiota population.

According to some embodiments, at least a portion of the plurality of bacterial genera is originated from the microbiota population. According to some embodiments, the microbiota population is a pre-determined targeted population of microbiota.

According to some embodiments, the composition comprises at least one or a subset of aerobic bacteria and at least one or a subset of anaerobic bacteria. According to some embodiments, the composition comprises at least one bacterial subset of bacteria in the form of biofilm and at least one bacterial subset of planktonic bacteria According to some embodiments, the composition comprises a plurality of bacterial genera having at least 30% similarity to a pre-determined targeted population of microbiota.

According to some embodiments, the composition comprises a plurality of bacterial genera having at least 30% similarity to a microbiota origin population.

According to some embodiments, the population of microbiota is selected from the group consisting of: a gut microbiota, a saliva microbiota, a skin microbiota, an oral microbiota, a bronchial microbiota, a vaginal microbiota, a soil microbiota, or a mixture thereof.

According to some embodiments, the plurality of bacterial genera is derived from one or more samples selected from the group consisting of: a fecal sample, a saliva sample, a skin sample, an oral sample, a bronchial sample, a vaginal sample, a soil sample, or a mixture thereof.

According to some embodiments, the population of microbiota is derived from at least one origin.

According to some embodiments, the plurality of bacterial genera is derived from one or more healthy mammal, animal donor, bacterial strain, stored microbiota sample, bacterial colony, planktonic sample and a biofilm.

According to some embodiments, the composition further comprises a plurality of particles.

According to some embodiments, wherein each particle comprises the co-culture of at least two distinct bacterial families.

According to another aspect, there is provided a pharmaceutical composition comprising the composition described herein and a pharmaceutically acceptable carrier or excipient.

According to some embodiments, the pharmaceutically acceptable carrier or excipient is selected from one or more of a stabilizer, a preservative, a chelating agent, a viscosity modifying agent, a buffering agent, and pH adjusting agent.

According to some embodiments, the pharmaceutical composition is formulated for rectal, intravenous, parenteral, mucosal, nasal or oral administration.

According to some embodiments, the pharmaceutical is for use in treatment of dysbiosis.

According to another aspect, there is provided a method of treating a disease or a disorder in a subject in need thereof, the method comprises administering to the subject the composition described herein. According to some embodiments, the said disease or disorder is dysbiosis.

According to another aspect, there is provided a method for obtaining a composition comprising a co-culture of at least two distinct bacterial families, having differing growth and/or proliferative conditions, the method comprising the steps of:

a. providing a plurality of bacterial genera comprising microbiota from at least one origin;
b. suspending said plurality of bacterial genera to receive a bacterial genera solution;
c. filtering the plurality of bacterial genera solution thereby obtaining a filtrate comprising the plurality of bacterial genera;

d. incubating the filtrate with a plurality of particles, and allowing the plurality of bacterial genera to attach to the plurality of particles;

e. dividing the plurality of bacterial genera of (d) into a plurality of bacterial solution subsets;

f. culturing each bacterial solution subset in a growth medium and under proliferative conditions suitable for the proliferative of the individual subset;

g. removing the growth medium, and recombining the individual subsets;

thereby obtaining the composition comprising a co-culture of at least two distinct bacterial families, having differing growth and/or proliferative conditions.

According to some embodiments, the proliferative conditions are selected from the group consisting of: aerobic, anaerobic, and microaerophilic conditions. According to some embodiments, the proliferative conditions are selected from flow, shake, and static conditions. According to some embodiments, the proliferative conditions are selected from moist conditions and low-humidity conditions.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description together with the drawings makes apparent to those skilled in the art how embodiments of the invention may be practiced.

In the drawings.

DETAILED DESCRIPTION OF THE INVENTION

Figure 1:
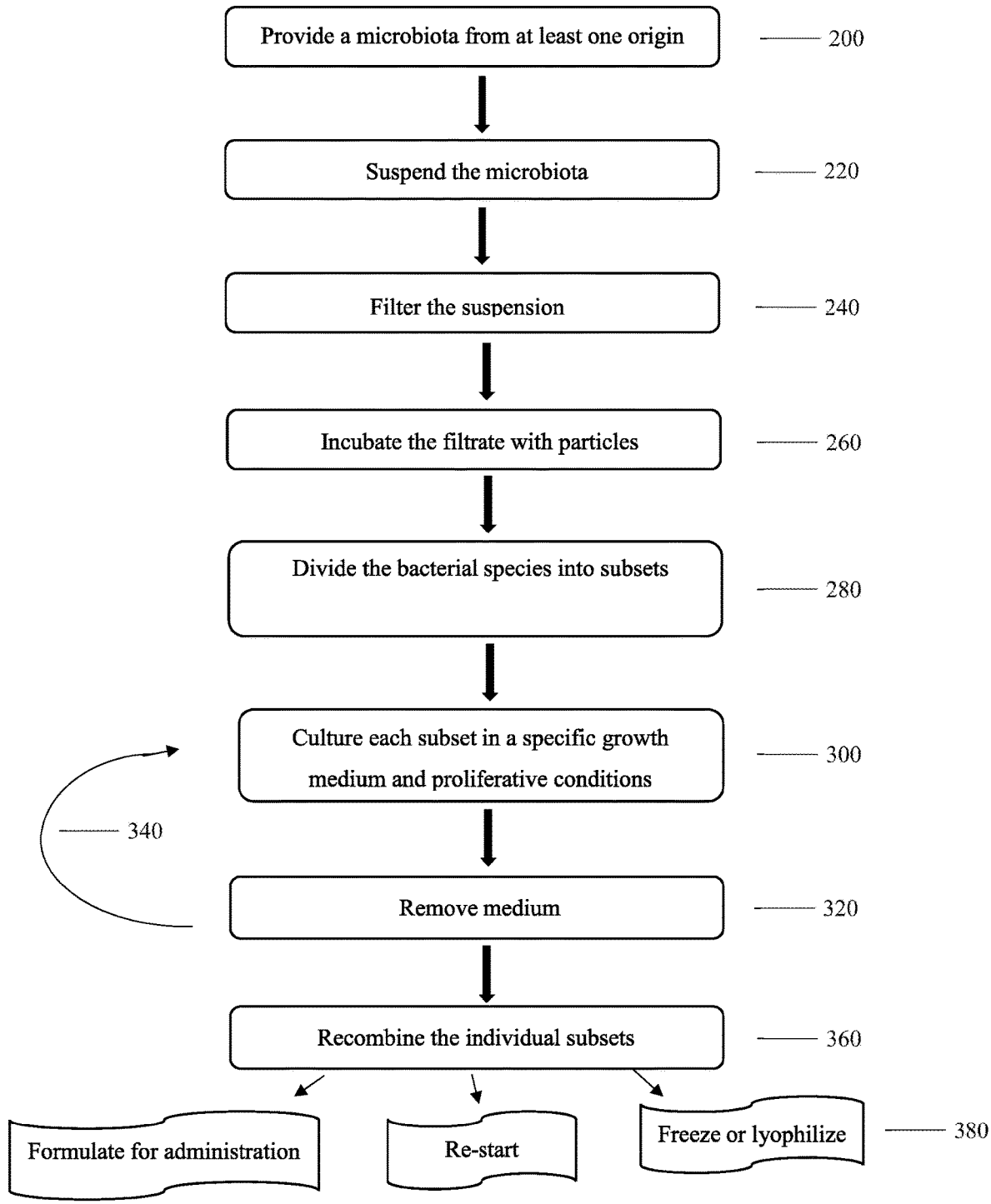
FIG. 1 is a flowchart demonstrating, as a non-limiting example, the steps for obtaining the microbiota composition.
Figure 2:
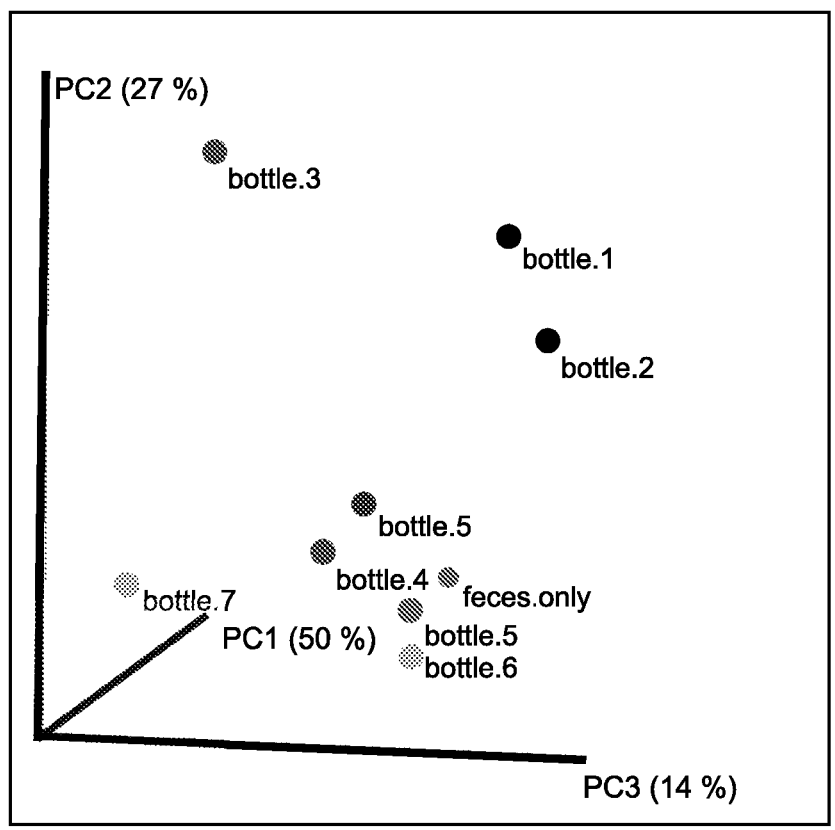
FIG. 2 presents the relative distribution of the bacteria cultured in the following conditions: Bottle 1. Aerobic liquid feces; Bottle 2. Aerobic TSB; Bottle 3. Aerobic RCM; Bottle 4. Aerobic fecal filtrate; Bottle 5. Anaerobic liquid feces; Bottle 6. Anaerobic TSB; Bottle 7. Anaerobic RCM; Bottle 8. Anaerobic fecal filtrate; Results are based on Principal Coordinate Analysis (PCoA) of weighted UniFrac distances based on 16s rRNA analysis of the microbial communities of each of the condition (bottle). The percentage of variation explained by the principal coordinates is indicated on the axes/

The present invention provides a composition comprising a plurality of bacterial genera and method of use thereof. In some embodiments, the composition of the invention comprises a plurality of bacterial genera having high similarity to a microbial flora.

In additional embodiments, the invention provides a composition comprising a co-culture of bacterial genera. In some embodiments, the co-culture of bacterial genera has high similarity to a microbial flora.

As used herein, the term "microbiota" or "microbial flora" refers to the collection of microbes (including but not limited to bacteria, fungi such as yeast, found, constitute or known to reside in an environmental niche. In some embodiments, the microbial flora is a collection of microbes found or known to reside in an environmental niche of a healthy subject. Non-limiting examples of environmental niches include gut, skin, saliva, oral and upper respiratory tract and urogenital tract. Additional non-limiting examples of environmental niches include soil, ground water, and open waters.

In some embodiments, the microbial flora has a common origin (i.e., are derived from a similar environmental niche). In some embodiments, the microbial flora has a common target. As described herein, the methods of the present invention may obtain various bacteria and form a synthetic composition with high identity or similarity to a targeted environmental niche. In some embodiments, the compositions of the invention comprise a plurality of bacterial genera having at least 30% similarity to a microbiota targeted-environmental niche.

In some embodiments, the bacterial genera of the composition are a synthetic assembly of bacterial co-culture, so as to resemble a microbial flora of a common origin (e.g., a predetermined environmental niche) or a designated bacterial co-culture.

In one embodiment, the composition of the invention comprises a co-culture of at least two distinct bacteria. In another embodiment, the composition of the invention comprises a co-culture of at least 3, at least 4, at least 5, at least 6, at least 7, at least 8, at least 9, at least 10, at least 15, at least 20, at least 25, at least 30, at least 35, at least 40, at least 45, or at least 50 distinct bacteria. In one embodiment, the distinct bacteria are bacteria from different families. In one embodiment, the distinct bacteria are bacteria from different genera. The term "distinct" refers to bacteria having differing growth and/or proliferative conditions. In one embodiment, the differing growth and/or proliferative conditions is at least two optimal conditions wherein a first condition allows substantially optimal growth proliferate and cultivation of a first bacteria and a second condition allowing substantially optimal growth proliferate and cultivation of a second bacteria.

In some embodiments, the bacterial co-culture of the invention comprises at least one or a subset of aerobic bacteria. In some embodiments, the bacterial co-culture of the invention comprises at least one or a subset of anaerobic bacteria. In some embodiments, the bacterial co-culture of the invention comprises at least one or a subset of aerobic bacteria and at least one or a subset of anaerobic bacteria.

In some embodiments, the bacterial co-culture of the invention comprises at least one or a subset of bacteria in the form of biofilm. In some embodiments, the bacterial co-culture of the invention comprises at least one or a subset of planktonic bacteria. In some embodiments, the bacterial co-culture of the invention comprises at least one or a subset of bacteria in the form of biofilm and at least one or a subset of planktonic bacteria.

In some embodiments, at least a portion of the co-culture is in syntrophic relationship.

As demonstrated herein below, the compositions formed under the processed described herein showed high similarity to gut bacterial genera (e.g., more than 90% similarity to the commonly known gut bacterial genera). Further, the compositions described herein showed high similarity to soil bacterial flora (more than 30% similarity to soils sample). Further, the compositions described herein showed high similarity to oral bacterial flora (more than 30% similarity to oral samples).

In some embodiments, the composition of the invention is a synthetic composition. As use herein, the term "synthetic" refers to a bacteria composition grown in-vitro under at least two different growth mediums and proliferative conditions.

In some embodiments, the microbiota is a gut microbiota. In some embodiments, the microbiota is an oral microbiota. In some embodiments, the microbiota is obtained from saliva. In some embodiments, the microbiota is a bronchial microbiota. In some embodiments, the microbiota is a skin microbiota. In some embodiments, the microbiota is a vaginal microbiota. In some embodiments, the microbiota is a soil microbiota.

In some embodiments, the plurality of bacterial genera is derived from a subject (such as a human). In some embodiments, the plurality of bacterial genera is derived from one or more samples selected from a fecal sample, a saliva sample, an oral sample, a bronchial sample, a skin sample, and a vaginal sample. In some embodiments, the plurality of bacterial genera is derived from a fecal sample. In some embodiments, the plurality of bacterial genera is derived from a saliva sample. In some embodiments, the plurality of bacterial genera is derived from an oral sample. In some embodiments, the plurality of bacterial genera is derived from a bronchial sample. In some embodiments, the plurality of bacterial genera is derived from skin sample. In some embodiments, the plurality of bacterial genera is derived from a vaginal sample.

The bacterial genera may be derived from a single sample or a plurality of samples. At least a portion of the bacterial genera may be derived from samples other than an animal. In some embodiments, the plurality of bacterial genera is derived from soil. In some embodiments, the plurality of bacterial genera is derived from a plant matter.

In some embodiments, the composition of soil microbiota is for agricultural use. In some embodiments, there is provided the composition as described herein and agriculturally acceptable carrier. In some embodiments, the composition of soil microbiota is useful in enhancing a desired plant trait. In some embodiments, the composition of soil microbiota is useful for the enhancing or improving plant growth. In some embodiments, the composition of soil microbiota is useful for pesticide degradation. In some embodiments, the composition of soil microbiota improves soil fertility. In some embodiments, the composition of soil microbiota is used to mediate nitrogen fixation, denitrification and nitrification due to the pivotal role of microbes in nitrogen cycling. In one embodiment, the plurality of bacterial genera is obtained from uncontaminated soil or water sample.

In some embodiments, the composition contains at least 20%, at least 25%, at least 30%, at least 40%, at least 45%, at least 50%, at least 60%, at least 70%, at least 80%, or at least 90%, at least 95%, at least 97%, at least 99% similarity, including any value therebetween, to an environmental niche.

In some embodiments, the composition of the invention comprises at least 20%, at least 25%, at least 30%, at least 40%, at least 45%, at least 50%, at least 60%, at least 70%, at least 80%, or at least 90%, at least 95%, at least 97%, at least 99% similarity, including any value therebetween, to an origin population of the microbiota.

In some embodiments, the composition contains at least 20%, at least 25%, at least 30%, at least 40%, at least 45%, at least 50%, at least 60%, at least 70%, at least 80%, or at least 90%, at least 95%, at least 97%, at least 99% similarity, including any value therebetween, to a target microbiota population.

In some embodiments, the composition contains at least 70% similarity to a population of gut microbiota. Table 8 lists a non-limiting example of gut microbiota.

In some embodiments, the composition contains at least 25% similarity to a population of soil microbiota. In some embodiments, the composition contains at least 30% similarity to a population of soil microbiota. Table 9 lists a non-limiting example of gut microbiota.

In some embodiments, the composition contains at least 25% similarity to a population of saliva microbiota. In some embodiments, the composition contains at least 30% similarity to a population of saliva microbiota. Table 11 lists a non-limiting example of gut microbiota.

In some embodiments, the population of microbiota is derived from at least one origin. In some embodiments, the population of microbiota is derived from a plurality of origins. In some embodiments, the population of microbiota is derived from at least 3, at least 4, at least 5 origins.

In some embodiments, the composition comprises at least 2, 3, 4, 5, 6, 7, 8, 9, 10, 11, 12, 13, 14, 15, 20, 25, 30, 35, 40, 45, 45, 50, 55, 60, 65, 70, 80, 90, 100 bacterial families, including any value therebetween. In some embodiments, the population of microbiota comprises at least 2, 4, 5, 6, 7, 8, 9, 10, 15, 20, 25, 30, 35, 40, 45, 50, 55, 60, 65, 70, 80, 90, 100 bacterial genera, including any value therebetween. In some embodiments, the composition comprises at least one population of bacterial genera In some embodiments, the composition of the invention comprises a plurality of pre-determined bacterial strains. The term "pre-determined" as used herein refers to a custom-made composition comprising bacterial strains selected according to a specific need. As exemplified herein, a composition comprising pre-determined bacterial strains may be designated by cultivating the microbiota using various growth media and proliferative conditions.

In some embodiments, the composition contains at least 20%, at least 25%, at least 30%, at least 40%, at least 45%, at least 50%, at least 60%, at least 70%, at least 80%, or at least 90%, at least 95% similarity to the microbiota population listed in Table 8, 9 or 11.

In some embodiments, the composition of a plurality of gut bacterial genera having at least 70% similarity to the list in Table 8.

In some embodiments, the composition of a plurality of soil bacterial families having at least 30% similarity to the list in Table 9.

In some embodiments, the composition of a plurality of oral bacterial families having at least 30% similarity to the list in Table 11.

In some embodiments, the composition comprises a bacterial co-cloture of one or more bacterias selected from Actinobacteria, Archea, Bacteroidetes, *Deinococcus-Thermus*, Firmicutes, Fusobacteria, Lentisphaerae, Proteobacteria, Synergistetes, Tenericutes, and Verrucomicrobia.

In one embodiment, the plurality of bacterial genera is obtained from a healthy mammal. In one embodiment, the plurality of bacterial genera is obtained from an animal donor. In one embodiment, the donor may be screened for their health status and nutrition habits. In one embodiment, the plurality of bacterial genera is derived from a bacterial strain. In some embodiments, the plurality of bacterial genera is derived from stored bacterial strain. In some embodiments, the plurality of bacterial genera is derived from freezed bacterial strain. In some embodiments, the plurality of bacterial genera is derived from freezed biofilm. In some embodiments, the plurality of bacterial genera is derived from lyophilized bacterial strain. In some embodiments, the plurality of bacterial genera is a probiotic strain.

As used herein, the term "probiotic" refers to a beneficial or required bacterial strain that can also stimulate the growth of other microorganisms, especially those with beneficial properties (such as those of the intestinal flora). In one embodiment, the plurality of bacterial genera is derived from a stored microbiota sample. In one embodiment, the plurality of bacterial genera is derived from a bacterial colony.

In one embodiment, at least a portion of the plurality of bacterial genera is derived from a biofilm. In one embodiment, at least a portion of the plurality of bacterial genera is derived from a planktonic sample.

According to some embodiments, the composition of the invention further comprises a plurality of particles. According to some embodiments, the particles are adapted, configured or suitable for biofilm formation. According to some embodiments, the plurality of particles comprises one or more types of particles selected from the group consisting of: seeds (e.g., passion fruit, nigella and pomegranate seeds), crushed seeds, grains, particles comprising bentonite clay particles, sand particles, white clay particles, particles comprising cellulose fibers, cellulose particles (e.g., microcrystalline cellulose (MCC)), dicalcium phosphate particles (DCP), agarose beads and any combination thereof. In one embodiment, one or more particles are porous.

In some embodiments, the plurality of particles is a synthetic scaffold.

In some embodiments, the seeds are selected from the group consisting of: pomegranate seeds, and passion fruit seeds. In some embodiments, the seeds are crushed.

In some embodiments, the particles range from 5 microns to 1 cm in diameter. In some embodiments, the particles are 5 microns in diameter. In some embodiments, the particles are 10 microns in diameter. In some embodiments, the particles are 15 microns in diameter. In some embodiments, the particles are 20 microns in diameter. In some embodiments, the particles are 30 microns in diameter. In some embodiments, the particles are 40 microns in diameter. In some embodiments, the particles are 50 microns in diameter. In some embodiments, the particles are 60 microns in diameter. In some embodiments, the particles are 70 microns in diameter. In some embodiments, the particles are 80 microns in diameter. In some embodiments, the particles are 90 microns in diameter. In some embodiments, the particles are 100 microns in diameter. In some embodiments, the particles are 200 microns in diameter. In some embodiments, the particles are 300 microns in diameter. In some embodiments, the particles are 400 microns in diameter. In some embodiments, the particles are 500 microns in diameter. In some embodiments, the particles are 600 microns in diameter. In some embodiments, the particles are 700 microns in diameter. In some embodiments, the particles are 800 microns in diameter. In some embodiments, the particles are 900 microns in diameter. In some embodiments, the particles are 1 cm in diameter.

Reference is made to FIG. 1 describing as a non-limiting example a method for obtaining the composition of the invention. First, a sample comprising a plurality of bacterial genera (e.g., microbiota from at least one target or origin population) is provided (step 200); subsequently, the plurality of bacterial genera is suspended to receive a bacterial genera solution (step 220). The bacterial sample may be diluted in any solution such as PBS which still maintains the bacteria natural surroundings and is suitable for growth of at least one bacterial. Dilution may be in any range which is suitable for growth of at least one bacterial genera, such as 1 gr sample: 1 mL solution-1 g sample-10 L solution, 1 gr sample:10 mL solution-1 g sample-5 L solution, or 1 gr sample:10 mL solution-1 g sample-1 L solution.

The plurality of bacterial genera solution may be filtered in order to obtain a filtrate containing the plurality of bacterial genera comprising the microbiota (step 240). The filtrate may be incubated with a plurality of particles, under conditions allowing for at least a portion of the plurality of bacterial genera to attach to the plurality of particles (step 260).

The plurality of bacterial genera attached to the plurality of particles is subsequently divided into a plurality of subsets of particles (to induce growth of biofilm) (step 280). Alternatively, at least one subset is taken from the bacterial solution (of step 220 or 240) which is devoid of particles (so as to induce growth of planktonic bacteria). Subsequently, a culturing step follows, wherein each individual subset is cultured in a growth medium and proliferative condition unique for the individual subset for a first period of time (step 300); subsequently, the first medium is removed, and a second culturing step may follow, wherein the individual subset is cultured in a growth medium and proliferative conditions for a second period of time (step 320); subsequently, the second growth medium is removed, and the individual subsets are combined to form the composition of the invention (step 340).

In some embodiments, at least one proliferative condition for a single subset includes an aerobic condition (presence of oxygen). In some embodiments, at least one proliferative condition for a single subset includes an anaerobic condition (absence of free or bound oxygen).

In some embodiments, at least one proliferative condition for a single subset includes a microaerophilic condition. In some embodiments, at least one proliferative condition for a single subset includes an airlift fermenter.

In some embodiments, at least one proliferative condition for a single subset includes biofilm growth conditions. In some embodiments, at least one proliferative condition for a single subset includes a static condition (without shaking, without any flow of medium, such that there is no shear force exerted on the bacteria). In some embodiments, at least one proliferative condition for a single subset includes planktonic growth conditions. In some embodiments, at least one proliferative condition for a single subset includes a flow condition (the medium flows in relation to the bacteria attached to the surface, such that the attached bacteria are subjected to shear force).

In some embodiments, at least one proliferative condition for a single subset includes a flow rate of at least 5, at least 6, at least 7, at least 8, at least 9, at least 10, at least 11, at least 12, at least 13, at least 14 or at least 15 ml/hr. In some embodiments, at least one proliferative condition for a single subset includes a flow rate of at most 30, at most 25, at most 20, at most 19, at most 18, at most 17, at most 16, at most 15, at most 14, at most 13, at most 12, at most 11 or at most 10 ml/hr.

In some embodiments, at least one proliferative condition for a single subset includes a flow rate in the range of about 5 to about 10 ml/hr. In some embodiments, at least one proliferative condition for a single subset includes a flow rate in the range of about 6 to about 10 ml/hr. In some embodiments, at least one proliferative condition for a single subset includes a flow rate in the range of about 7 to about 10 ml/hr. In some embodiments, at least one proliferative condition for a single subset includes a flow rate in the range of about 8 to about 10 ml/hr. In some embodiments, at least one proliferative condition for a single subset includes a flow rate in the range of about 6 to about 12 ml/hr. In some embodiments, at least one proliferative condition for a single subset includes a flow rate in the range of about 7 to about 12 ml/hr. In some embodiments, at least one proliferative condition for a single subset includes a flow rate in the range of about 8 to about 12 ml/hr. In some embodiments, at least one proliferative condition for a single subset includes a flow rate in the range of about 9 to about 12 ml/hr. In some embodiments, at least one proliferative condition for a single subset includes a flow rate in the range of about 10 to about 12 ml/hr. In some embodiments, at least one proliferative condition for a single subset includes a flow rate in the range of about 10 to about 14 ml/hr. In some embodiments, at least one proliferative condition for a single subset includes a flow rate in the range of about 11 to about 14 ml/hr. In some embodiments, at least one proliferative condition for a single subset includes a flow rate in the range of about 12 to about 14 ml/hr. In some embodiments, at least one proliferative condition for a single subset includes a flow rate in the range of about 12 to about 15 ml/hr. In some embodiments, at least one proliferative condition for a single subset includes a flow rate in the range of about 15 to about 20 ml/hr. In some embodiments, at least one proliferative condition for a single subset includes a flow rate in the range of about 15 to about 18 ml/hr. In some embodiments, at least one proliferative condition for a single subset includes a flow rate in the range of about 17 to about 20 ml/hr. In some embodiments, at least one proliferative condition for a single subset includes a flow rate in the range of about 20 to about 23 ml/hr. In some embodiments, at least one proliferative condition for a single subset includes a flow rate in the range of about 22 to about 25 ml/hr. In some embodiments, t at least one proliferative condition for a single subset includes a flow rate in the range of about 25 to about 30 ml/hr. In some embodiments, at least one proliferative condition for a single subset includes a flow rate in the range of about 10 to about 20 ml/hr. In some embodiments, at least one proliferative condition for a single subset includes a flow rate in the range of about 5 to about 15 ml/hr. In some embodiments, at least one proliferative condition for a single subset includes a flow rate in the range of about 15 to about 30 ml/hr.

In some embodiments, at least one proliferative condition for a single subset includes a shaking condition. In some embodiments, at least one proliferative condition for a single subset includes shaking by a tilt shaker. In some embodiments, at least one proliferative condition for a single subset includes shaking at about 80, 90, 100, 120, 140, 150, 160, 180, 200, 210, 220, 230, 240, 250, 260, 280, 300, 350, 400, 450, 500 rpm, or any value therebetween. In one embodiment, at least one proliferative condition for a single subset includes shaking at about 100 rpm. In one embodiment, at least one proliferative condition for a single subset includes shaking at about 150 rpm. In one embodiment, at least one proliferative condition for a single subset includes shaking at about 180 rpm. In one embodiment, at least one proliferative condition for a single subset includes shaking at about 230 rpm. In one embodiment, at least one proliferative condition for a single subset includes shaking at about 240 rpm. In one embodiment, at least one proliferative condition for a single subset includes shaking at about 250 rpm. In one embodiment, at least one proliferative condition for a single subset includes shaking at about 260 rpm.

In some embodiments, at least one proliferative condition for a single subset includes shaking for about 30 minutes. In some embodiments, at least one proliferative condition for a single subset includes shaking for 1, 2, 3, 4, 5, 6, 10, 12, 15 hours or any value therebetween. In some embodiments, at least one proliferative condition for a single subset includes overnight shaking. In some embodiments, at least one proliferative condition for a single subset includes shaking for 1, 2, 3, 4, 5, 6, 7, 10 days. In some embodiments, at least one proliferative condition for a single subset includes shaking for 1 day. In some embodiments, at least one proliferative condition for a single subset includes shaking for 4 days. In some embodiments, at least one proliferative condition for a single subset includes shaking for 7 days.

In some embodiments, the incubation time of the proliferative conditions is 1, 2, 3, 4, 5, 6, 10, 12, 15 hours or any value therebetween. In some embodiments, the incubation time of the proliferative conditions is overnight. In some embodiments, the incubation time of the proliferative conditions is at least 1, 2, 3, 4, 5, 6, 7, 10 days. In some embodiments, the incubation time of the proliferative conditions is at most 2, 3, 4, 5, 6, 7, 10 days. In some embodiments, the incubation time of the proliferative conditions is at least 1 day. In some embodiments, the incubation time of the proliferative conditions is at least 4 days. In some embodiments, the incubation time of the proliferative conditions is at least 7 days.

In some embodiments, at least one proliferative condition for a single subset includes a pH gradient as known in the origin tissue. In some embodiments, at least one proliferative condition for a single subset includes pH in the range of between about 6.6 to about 7.5 or any value therebetween. In some embodiments, at least one proliferative condition for a single subset includes pH in the range of between about 5.6 to about 7.9 or any value therebetween. In some embodiments, at least one proliferative condition for a single subset includes pH in the range of between about 4.5 to about 8 or any value therebetween. In some embodiments, at least one proliferative condition for a single subset includes pH in the range of between about 4.0 to about 7.0 or any value therebetween. In some embodiments, at least one proliferative condition for a single subset includes pH in the range of between about 3.0 to about 4.5 or any value therebetween. In some embodiments, at least one proliferative condition for a single subset includes pH in the range of between about 7.0 to about 7.5 or any value therebetween. In some embodiments, at least one proliferative condition for a single subset includes pH in the range of between about 7.0 to about 7.4 or any value therebetween. In some embodiments, at least one proliferative condition for a single subset includes pH above 5.5. In some embodiments, at least one proliferative condition for a single subset includes pH in the range of between about 3.0 to about 10.0 or any value therebetween. In some embodiments, at least one proliferative condition for a single subset includes pH in the range of between about 5.5 to about 7.5 or any value therebetween.

In one embodiment, the plurality of bacterial genera is configured for pH dependent targeted release in the gastrointestinal tract. In one embodiment, the composition is configured to release at least one bacterial strain at a pH found in the intestine.

In some embodiments, the composition can colonize the gut in the range of at least about $2 \times 10^2$ to about $2 \times 10^{10}$ bacteria per gram each day for at least 5 days after administration.

In some embodiments, at least one proliferative condition for mammalian microbiota is temperature in the range of between about 30° C. to about 40° C. or any value therebetween. In some embodiments, at least one proliferative condition for soil microbiota is temperature in the range of between about 15° C. to about 25° C. or any value therebetween. In some embodiments, the proliferative condition for a single subset includes temperature in the range of between about 15° C. to about 20° C. or any value therebetween. In some embodiments, the proliferative condition for a single subset includes temperature in the range of between about 20° C. to about 30° C. or any value therebetween. In some embodiments, the proliferative condition for a single subset includes temperature in the range of between about 30° C. to about 37° C. or any value therebetween. In some embodiments, the proliferative condition for a single subset includes temperature in the range of between about 40° C. to about 55° C. or any value therebetween. In some embodiments, the proliferative condition for a single subset includes temperature in the range of between about 50° C. to about 60° C. or any value therebetween. In some embodiments, the proliferative condition for a single subset includes temperature in the range of between about 5° C. to about 37° C. or any value therebetween. In some embodiments, the proliferative condition for soil microbiota is temperature in the range of between about 30° C. to about 75° C. or any value therebetween. In one embodiment, the proliferative condition for a single subset includes a temperature of about 30° C. In one embodiment, the proliferative condition for a single subset includes a temperature of about 37° C. In some embodiments, the proliferative conditions for a single subset includes moist conditions. In some embodiments, the proliferative conditions for a single subset includes low-humidity conditions.

In some embodiments, at least one proliferative condition for a single subset includes ultraviolet (UV) exposure. In some embodiments, at least one proliferative condition for a single subset includes the presence of high NaCl concentrations as 2-3% w/v.

In one embodiment, the proliferative conditions for a single subset includes anaerobic conditions. The term "anaerobic condition" refers to an atmosphere that contains less than 5 ppm (part per million) of oxygen, preferably less than 0.5 ppm of oxygen, and more preferably less than 0.1 ppm of oxygen. Any suitable method can be used to provide the desired anaerobic condition or atmosphere.

In one embodiment, the proliferative conditions for a single subset includes static and anaerobic conditions. In one embodiment, the proliferative conditions for a single subset includes static and aerobic conditions. In one embodiment, the proliferative conditions for a single subset includes flow and anaerobic conditions. In one embodiment, the proliferative conditions for a single subset includes flow and aerobic conditions. In one embodiment, the proliferative conditions for a single subset includes pH in the range of 6.6-7.5 and static and anaerobic conditions. In one embodiment, the proliferative conditions for a single subset includes pH in the range of 6.6-7.5 and flow and anaerobic conditions. In one embodiment, the proliferative conditions for a single subset includes pH in the range of 6.6-7.5 and shaking and anaerobic conditions. In one embodiment, the proliferative conditions for a single subset includes pH in the range of 6.6-7.5 and shaking and aerobic conditions. In one embodiment, the proliferative conditions for a single subset includes shaking and planktonic growth conditions. In one embodiment, the proliferative conditions for a single subset includes shaking and biofilm growth conditions. In one embodiment, the proliferative conditions for a single subset includes shaking and biofilm growth conditions at about 30° C. In one embodiment, the proliferative conditions for a single subset includes shaking and biofilm growth conditions at about 37° C. In one embodiment, the proliferative conditions for a single subset includes shaking and planktonic growth conditions at about 30° C. In one embodiment, the proliferative conditions for a single subset includes shaking and planktonic growth conditions at about 37° C. In one embodiment, the proliferative conditions for a single subset includes shaking and planktonic growth conditions at about 15-25° C. In one embodiment, the proliferative conditions for a single subset includes shaking and biofilm growth conditions at about 15-25° C. In one embodiment, the proliferative conditions for a single subset includes aerobic and biofilm growth conditions at about 30° C. In one embodiment, the proliferative conditions for a single subset includes aerobic and biofilm growth conditions at about 37° C. In one embodiment, the proliferative conditions for a single subset includes aerobic and planktonic growth conditions at about 30° C. In one embodiment, the proliferative conditions for a single subset includes aerobic and planktonic growth conditions at about 37° C.

In some embodiments, the origin microbiota may be suspended in saline (step 220) and filtered prior to culturing in order to get rid of at least some of unnecessary solids (step 240). In some embodiments, the sample comprising the origin microbiota may be sterilized such as to remove pathogens (step 240).

In some embodiments, the plurality of bacterial genera may be cultured with antibiotics, bacteriophage, competing bacteria or any other method that will reduce growth of a certain population to allow more genera to grow or enhance other characteristics capabilities as biofilm (step 300 or 260 in FIG. 1). In some embodiments, the plurality of bacterial genera may be cultured with specific antibiotics against *Lactobacillus plantarum* (step 300 or 260 in FIG. 1) such as penicillin, or specifically carboxypenicillin (e.g., carbenicillin). One skilled in the art is capable of determining the specific type and dose of an antibiotics to be used against specific bacteria.

In some embodiments, changing the growth medium and proliferative conditions to each individual subset can be a repetitive step (step 340: step 320 and 300 in FIG. 1). In some embodiments, the plurality of subsets of particles is combined after culturing (step 360 in FIG. 1). In some embodiments, the plurality of subsets of particles is not combined after culturing for a specific formula.

In some embodiments, the composition may be further subjected to an expansion step, such as a starter for a new culture (re-inoculating with particles) (step 380). In some embodiments, the composition is stored by freezing (step 380). In some embodiments, the composition comprises a freezing buffer. In some embodiments, the composition is stored by lyophilization (step 380). In some embodiments, the composition comprises a drying buffer for lyophilization. In some embodiments, the drying buffer for lyophilization comprises e.g., 10% sucrose, protein, skim milk, maltose, mannose, etc. (in a non-limiting fashion) for longer shelf life and transportation. In some embodiments, the composition comprises microbiota combined with a synthetic liquid, for reconstitution of either freezing or freeze drying into a powder, or equivalent, before delivery to the patient.

The growth medium may be any known or commercially available growth medium, or otherwise may be synthesized to provide growth and proliferation of specific bacterial strains. Non-limiting examples of growth media includes: Tryptic soy broth (TSB), Robertson's Cooked Meat, Reinforced clostridium medium (RCM) broth, nutrient broth, Lysogeny broth (LB), ¼ LB, Heart infusion broth, Wilkins-Chalgren broth, *Brucella* broth, wheat bran, Brain heart infusion agar (BHI1), M9 minimal media or 0.2×BHI, Gut Microbiota Medium (GMM), Columbia blood agar (CBA), Chocolate agar (CHOC), Tryptic soy agar (TSY), Fastidious anaerobe agar (FAA), Cooked meat agar (BEEF), *Bifidobacterium* Selective Media (BSM), Phenylethyl alcohol agar (PEA), *Actinomyces* isolation agar (AIA), Colistin naladixic acid agar (CNA), McKay agar (MK), Mannitol slat agar (MSA), de Man Rogosa Sharpe agar (MRS), *Bacteroides* bile esculin agar (BBE), Deoxycholate agar (DOC), MacConkey agar (MAC), and Kanamycin vancomycin laked blood agar (KVLB).

In some embodiments, the growth medium is selected from the group consisting of tryptic soy broth (TSB), Robertson's Cooked Meat, Reinforced clostridium medium (RCM) broth, nutrient broth, Lysogeny broth (LB), ¼ LB, Heart infusion broth, Wilkins-Chalgren broth, *Brucella* broth, brain-heart infusion medium (BHI), wheat bran, or a combination thereof. In some embodiments, a specific growth medium may be used for enriching a specific bacterial genera or population for example, but not limited to, de man, rogosa and sharpe (MRS) agar for the enrichment of *Lactobacillus*. In some embodiments, the growth medium includes a dried unviable biofilm.

In some embodiments, the growth medium may also comprise materials that encourage the attachment of the bacteria to surfaces, or to encourage the creation of biofilm. In some embodiments, the growth medium may also comprise materials that reduce bacteria proliferation as antibiotics, bacteriophage, competing bacteria or any other method that will reduce a certain population to allow more genera to grow.

In some embodiments, the composition prevents the growth of one, or more than one pathogenic bacterial species in the patient. In one embodiment, the composition kills one, or more than one pathogenic bacterial species in the patient.

In some embodiments, the present invention provides a composition and method, comprising at least one population of a bacterial genera isolated from a plurality of bacterial genera. One skilled in the art may determine the bacterial constituents of the composition of the invention by sequencing of 16S ribosomal RNA or the detection of specific DNA probes.

In some embodiments, the microbiota from at least one origin is first treated for biological hazard, such as viruses, parasites, and the like.

According to another aspect of embodiments of the invention, there is provided a pharmaceutical composition in an embodiment thereof and a pharmaceutically acceptable carrier.

In some embodiments, the composition can be administered for treating a medical condition associated with any disease, medical condition, or disorder as described herein throughout in a subject in need thereof. In some embodiments, the composition may be provided per se or as part of a pharmaceutical composition. In some embodiments, the present invention provides a method for treatment of a disease or a disorder by administering the composition. In some embodiments, the composition is used for treatment for inflammatory bowel disease, chronic fatigue syndrome, small bowel bacterial overgrowth syndrome, obesity, cancer, bacterial vaginosis, colitis, diabetes, depression, constipation, and the like, in a non-limiting fashion.

As used herein, a "pharmaceutical composition" refers to a preparation of the composition described herein with other chemical components such as physiologically suitable carriers and excipients. Such carriers enable the pharmaceutical composition to be formulated as tablets, pills, dragees, capsules, liquids, gels, syrups, slurries, suspensions, and the like, for oral ingestion by a patient. The purpose of a pharmaceutical composition is to facilitate administration of a compound to an organism. Herein, the term "excipient" and "pharmaceutically acceptable agent" are used interchangeably and refer to at least one inert substance added to a pharmaceutical composition to further facilitate administration of the composition selected from, but not limited to: a stabilizer, a preservative, a chelating agent, a viscosity modifying agent, a buffering agent, and pH adjusting agent. Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, intraperitoneal, intracardiac, intranasal, or intraocular injections. In one embodiment, the composition is formulated for rectal administration. In one embodiment, the composition is formulated for oral administration. In one embodiment, the composition is formulated for local administration. In one embodiment, the composition is formulated for systemic administration. Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

General

As used herein the term "about" refers to ±10%.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples which, together with the above descriptions, illustrate the invention in a non-limiting fashion.

Example 1

Culturing Fecal-Derived Bacteria on Particles 100 gr of fresh feces was mixed with 600 ml saline solution in a blender. The mixture was filtered once through strainer and then twice more through Gauze pad. A small part of the filtrate was kept in −20° C. A particles mix was prepared containing equal amounts of: pomegranate seeds, passion fruit seeds and di-calcium phosphate (DCP) Nigella.

10 g of the mixture were inserted into 8 bottles, each containing 60 ml of filtered fresh feces. Four of the bottles were incubated in aerobic conditions (bottles 1-4) at 37° C., and the remaining 4 bottles were incubated in anaerobic conditions (bottles 5-8) at 37° C. for 7 days.

Bottle Treatments:

Bottles 1 and 5:

After 7 days of incubation the feces liquid was taken out, and the matrix was gently washed twice (once with 25 ml and the second time with 10 ml sterile PBSX1). The bottles were vortexed 3 times for 30 seconds and a sample from the liquid was taken to 16S ribosomal RNA (rRNA) sequencing.

Bottles 2 and 6:

After 7 days of incubation, 60 ml tryptic soy broth (TSB) was added and the bottles were incubated for 7 more days. The growth medium was taken out, and the matrix was gently washed twice (once with 25 ml and the second time with 10 ml sterile PBSX1). The bottles were vortexed 3 times for 30 seconds and a sample from the liquid was taken to 16S rRNA sequencing.

Bottles 3 and 7:

After 7 days of incubation, 60 ml of reinforced clostridium medium (RCM) broth was added and the bottles were incubated for 7 more days. The growth medium was taken out, and the matrix was gently washed twice (once with 25 ml and the second time with 10 ml sterile PBSX1). The bottles were vortexed 3 times for 30 seconds and a sample from the liquid was taken to 16S rRNA sequencing.

Bottles 4 and 8:

After 7 days of incubation, 60 ml sterile feces (feces filtrate that was filtered through filter of 0.2 μm) broth was added and the bottles were incubated for 7 more days. The growth medium was taken out, and the matrix was gently washed twice (once with 25 ml and the second time with 10 ml sterile PBSX1). The bottles were vortexed 3 times for 30 seconds and a sample from the liquid was taken to 16S rRNA sequencing.

Preparation for Sequencing:

2 ml sample from each bottle (after second wash and vortex) was centrifuges for 2 min at 14000 rpm. The supernatant was removed, and 100 μl of sterile PBSX1 was added to the sample and the DNA was purified from each sample.

Grow Bacteria Inflow:

After static growth of feces bacteria with the particles according to the above protocol, the particles were transferred from bottles 1 and 5 to a glass column with a combination of growth mediums (as listed above) at a flow rate of 10-12 ml/hour for 7 days in anaerobic conditions or aerobic conditions. A sample was taken, washed with PBSX1 and sequenced.

The results are shown in tables 1-7 which include quantifications of microorganisms at various phylogenetic levels that were present in the starting material (fecal sample) and in the compositions cultured according to some embodiments of the present invention, but were present in the fecal sample.

TABLE 1 microorganisms found in each growth condition with a stringent (minimum of 45 copies) cut-off.

| | Phylum | Family | Genera | Bottle 2 | Bottle 3 | Bottle 4 | Bottle 6 | Bottle 7 | Bottle 8 |
|---|---|---|---|---|---|---|---|---|---|
| 1 | Proteobacteria | Enterobacteriaceae | – | + | + | + | + | + | + |
| 2 | Firmicutes | Ruminococcaceae | – | + | + | + | + | + | + |
| 3 | Firmicutes | Clostridiales (order) | – | + | + | + | + | + | + |
| 4 | Firmicutes | Lachnospiraceae | – | + | + | + | + | + | + |
| 5 | Actinobacteria | Coriobacteriaceae | Collinsella | + | + | + | + | + | + |
| 6 | Actinobacteria | Coriobacteriaceae | – | + | + | + | + | + | + |
| 7 | Verrucomicrobia | Verrucomicrobiaceae | Akkermansia | + | | + | + | + | + |
| 8 | Euryarchaeota (Archea) | Methanobacteriaceae | Methanobrevibacter | + | | + | + | + | + |
| 9 | Bacteroidetes | Prevotellaceae | Prevotella | + | | + | + | + | + |
| 10 | Firmicutes | Lachnospiraceae | Ruminococcus | + | | + | + | + | |
| 11 | Firmicutes | Veillonellaceae | Phascolarctobacterium | + | + | + | + | | + |
| 12 | Firmicutes | Enterococcaceae | Enterococcus | + | + | + | + | | + |
| 13 | Firmicutes | Leuconostocaceae | – | + | + | + | + | | + |
| 14 | Actinobacteria | Coriobacteriaceae | Slackia | + | + | + | + | + | |
| 15 | Actinobacteria | Bifidobacteriaceae | Bifidobacterium | + | + | + | + | + | |
| 16 | Firmicutes | Lachnospiraceae | Blautia | + | | | + | + | + |
| 17 | Firmicutes | Ruminococcaceae | Faecalibacterium | + | | | + | + | + |
| 18 | Bacteroidetes | Bacteroidaceae | Bacteroides | | | + | + | + | |
| 19 | Firmicutes | Clostridiales (order) | Other | + | | + | | + | |
| 20 | Firmicutes | Lachnospiraceae | Coprococcus | | | | + | + | + |
| 21 | Firmicutes | Ruminococcaceae | Ruminococcus | | + | | | | + |
| 22 | Proteobacteria | Enterobacteriaceae | Citrobacter | | | | + | | + |
| 23 | Firmicutes | Clostridiaceae | – | | | + | + | | |
| 24 | Bacteroidetes | S24-7 | – | | | | + | + | |
| 25 | Bacteroidetes | – | – | | | | + | + | |
| 26 | Bacteroidetes | Porphyromonadaceae | Parabacteroides | | | | | + | |
| 27 | Firmicutes | Lachnospiraceae | Other | | | | | + | |
| 28 | Bacteroidetes | Rikenellaceae | – | | | | + | | |
| 29 | Firmicutes | Lachnospiraceae | Dorea | | | | | + | |
| 30 | Firmicutes | Streptococcaceae | Streptococcus | | | | | | |
| 31 | Actinobacteria | Coriobacteriaceae | Adlercreutzia | | | | | | |

The '+' sign represents the presence of the genera in a certain bottle. Out of the 31 genera that were present in the feces, only 2 genera did not appear in any of the bottles. This indicates 93% similarity to the original feces sample after combination of the various bottles.

TABLE 2 microorganisms found in each growth condition with a relaxed (all results) cut-off.

| | Phylum | Family | Genera | Bottle 2 | Bottle 3 | Bottle 4 | Bottle 6 | Bottle 7 | Bottle 8 |
|---|---|---|---|---|---|---|---|---|---|
| 1 | Firmicutes | Veillonellaceae | Acidaminococcus | + | + | + | + | + | + |
| 2 | Firmicutes | Lactobacillaceae | Lactobacillus | + | + | + | + | + | + |
| 3 | Euryarchaeota (Archea) | Methanobacteriaceae | Methanobrevibacter | + | + | + | + | + | + |
| 4 | Proteobacteria | Enterobacteriaceae | – | + | + | + | + | + | + |
| 5 | Firmicutes | Veillonellaceae | Dialister | + | + | + | + | + | + |

TABLE 2-continued microorganisms found in each growth condition with a relaxed (all results) cut-off.

| | Phylum | Family | Genera | Bottle 2 | Bottle 3 | Bottle 4 | Bottle 6 | Bottle 7 | Bottle 8 |
|---|---|---|---|---|---|---|---|---|---|
| 6 | *Bacteroidetes* | *Prevotellaceae* | *Prevotella* | + | + | + | + | + | + |
| 7 | *Proteobacteria* | *Alcaligenaceae* | *Sutterella* | + | + | + | + | + | + |
| 8 | *Firmicutes* | *Ruminococcaceae* | – | + | + | + | + | + | + |
| 9 | *Bacteroidetes* | *Paraprevotellaceae* | – | + | + | + | + | + | + |
| 10 | *Actinobacteria* | *Coriobacteriaceae* | – | + | + | + | + | + | + |
| 11 | *Firmicutes* | *Lachnospiraceae* | *Ruminococcus* | + | + | + | + | + | + |
| 12 | *Firmicutes* | *Enterococcaceae* | *Enterococcus* | + | + | + | + | + | + |
| 13 | *Firmicutes* | *Lachnospiraceae* | – | + | + | + | + | + | + |
| 14 | *Firmicutes* | *Clostridiales* (order) | – | + | + | + | + | + | + |
| 15 | *Actinobacteria* | *Coriobacteriaceae* | *Collinsella* | + | + | + | + | + | + |
| 16 | *Firmicutes* | *Clostridiales* (order) | – | + | + | + | + | + | + |
| 17 | *Firmicutes* | *Leuconostocaceae* | – | + | + | + | + | + | + |
| 18 | *Firmicutes* | *Veillonellaceae* | *Phascolarctobacterium* | + | + | + | + | + | + |
| 19 | *Firmicutes* | *Lachnospiraceae* | *Blautia* | + | + | + | + | + | + |
| 20 | *Firmicutes* | *Ruminococcaceae* | *Oscillospira* | + | + | + | + | + | + |
| 21 | *Verrucomicrobia* | *Verrucomicrobiaceae* | *Akkermansia* | + | + | + | + | + | + |
| 22 | *Actinobacteria* | *Bifidobacteriaceae* | *Bifidobacterium* | + | + | + | + | + | + |
| 23 | *Firmicutes* | *Ruminococcaceae* | *Faecalibacterium* | + | + | + | + | + | + |
| 24 | *Actinobacteria* | *Coriobacteriaceae* | *Slackia* | + | + | + | + | + | + |
| 25 | *Firmicutes* | *Ruminococcaceae* | *Ruminococcus* | + | + | + | + | + | + |
| 26 | *Firmicutes* | *Lachnospiraceae* | *Coprococcus* | + | + | + | + | + | + |
| 27 | *Firmicutes* | *Lachnospiraceae* | *Dorea* | + | + | + | + | + | + |
| 28 | *Proteobacteria* | *Enterobacteriaceae* | *Citrobacter* | + | + | + | + | + | + |
| 29 | *Bacteroidetes* | S24-7 | – | + | + | + | + | + | + |
| 30 | *Firmicutes* | *Lactobacillales* (order) | – | + | + | + | + | + | + |
| 31 | *Firmicutes* | *Clostridiaceae* | – | + | + | + | + | + | + |
| 32 | *Firmicutes* | *Erysipelotrichaceae* | *Catenibacterium* | + | + | + | + | + | + |
| 33 | *Firmicutes* | *Lachnospiraceae* | Other | + | + | + | + | + | + |
| 34 | *Firmicutes* | *Streptococcaceae* | *Streptococcus* | + | + | + | + | + | + |
| 35 | *Bacteroidetes* | *Rikenellaceae* | – | + | + | + | + | + | + |
| 36 | *Bacteroidetes* | *Bacteroidales* (order) | – | + | + | + | + | + | + |
| 37 | *Firmicutes* | *Enterococcaceae* | Other | + | + | + | + | + | + |
| 38 | *Firmicutes* | *Streptococcaceae* | *Lactococcus* | + | + | + | + | + | + |
| 39 | *Firmicutes* | *Turicibacteraceae* | *Turicibacter* | + | + | + | + | + | + |
| 40 | *Firmicutes* | *Veillonellaceae* | *Veillonella* | + | + | + | + | + | + |
| 41 | *Bacteroidetes* | *Bacteroidaceae* | *Bacteroides* | + | + | + | + | + | + |
| 42 | *Firmicutes* | *Mogibacteriaceae* | – | + | + | + | + | + | |
| 43 | *Firmicutes* | *Lachnospiraceae* | *Lachnospira* | + | + | | + | + | + |
| 44 | *Actinobacteria* | *Coriobacteriaceae* | *Eggerthella* | + | + | + | + | | + |
| 45 | *Actinobacteria* | *Coriobacteriaceae* | *Adlercreutzia* | + | + | + | + | | + |
| 46 | *Bacteroidetes* | *Porphyromonadaceae* | *Parabacteroides* | + | + | + | + | + | |
| 47 | *Firmicutes* | *Lachnospiraceae* | *Lachnobacterium* | + | | + | + | + | + |
| 48 | *Proteobacteria* | *Desulfovibrionaceae* | *Desulfovibrio* | | + | + | + | + | + |
| 49 | *Firmicutes* | *Christensenellaceae* | – | + | + | | + | + | |
| 50 | *Firmicutes* | *Lachnospiraceae* | *Roseburia* | + | | + | + | | + |
| 51 | *Firmicutes* | *Dehalobacteriaceae* | *Dehalobacterium* | + | + | + | | + | + |
| 52 | *Cyanobacteria* | *Streptophyta* (order) | – | + | | + | + | + | |
| 53 | *Firmicutes* | *Clostridiaceae* | Other | + | + | | + | + | |
| 54 | *Bacteroidetes* | *Barnesiellaceae* | – | + | | + | + | + | |
| 55 | *Firmicutes* | *Veillonellaceae* | *Megasphaera* | + | + | | + | + | |
| 56 | *Firmicutes* | *Erysipelotrichaceae* | *Eubacterium* | + | + | + | | | |
| 57 | *Tenericutes* | *Anaeroplasmataceae* | *Anaeroplasma* | + | | + | | + | |
| 58 | *Firmicutes* | *Lachnospiraceae* | *Anaerostipes* | | | | + | + | + |
| 59 | *Firmicutes* | *Erysipelotrichaceae* | – | | | + | | + | + |
| 60 | *Actinobacteria* | *Actinomycetaceae* | *Actinomyces* | | | + | + | + | |
| 61 | *Proteobacteria* | *Desulfovibrionaceae* | *Bilophila* | | | | + | + | + |
| 62 | *Firmicutes* | *Veillonellaceae* | *Megamonas* | | | | + | | + |
| 63 | *Proteobacteria* | *Enterobacteriaceae* | *Trabulsiella* | + | | + | | | |
| 64 | *Bacteroidetes* | *Odoribacteraceae* | *Odoribacter* | | | | | + | |
| 65 | *Bacteroidetes* | *Paraprevotellaceae* | *Paraprevotella* | | | | | | |
| 66 | *Bacteroidetes* | *Paraprevotellaceae* | *Prevotella* | | | | | | |
| 67 | *Tenericutes* | RF39 (order) | – | | | | | | |
| 68 | *Proteobacteria* | *Pasteurellaceae* | *Haemophilus* | | | | | | |

The '+' sign represents the presence of the genera in a certain bottle. Out of the 68 genera that appeared in the original feces, only 4 genera did not appear in any of the bottles. This indicates 94% similarity to the original feces sample.

TABLE 3

Phylum distribution in the different bottles, each grown in different conditions. The numbers represent the % of a specific phylum in the bacterial population of the bottle.

| Phylum | bottle.2 | bottle.3 | bottle.4 | bottle.6 | bottle.7 | bottle.8 | Original feces |
|---|---|---|---|---|---|---|---|
| *Euryarchaeota* | 0.0362 | 0.000174 | 0.005728 | 0.043009 | 0.004738 | 0.023296 | 0.121371 |
| *Actinobacteria* | 0.011255 | 0.051137 | 0.019861 | 0.02041 | 0.007511 | 0.011519 | 0.04217 |
| *Bacteroidetes* | 0.0333 | 0.001174 | 0.277208 | 0.188729 | 0.206208 | 0.265022 | 0.04493 |
| *Firmicutes* | 0.865729 | 0.585984 | 0.640651 | 0.638442 | 0.577003 | 0.596923 | 0.260076 |
| *Proteobacteria* | 0.052076 | 0.361286 | 0.052595 | 0.102764 | 0.201088 | 0.095246 | 0.217608 |
| *Tenericutes* | 1.08E−05 | 0 | 0.000138 | 0 | 0.002337 | 0 | 0.000595 |
| *Verrucomicrobia* | 0.001429 | 0.000244 | 0.003819 | 0.006645 | 0.001115 | 0.007994 | 0.313251 |

TABLE 4

Class distribution in the different bottles, each grown in different conditions. The numbers represent the % of a specific phylum in the bacterial population of the bottle.

| Class | bottle.2 | bottle.3 | bottle.4 | bottle.6 | bottle.7 | bottle.8 | Original feces |
|---|---|---|---|---|---|---|---|
| *Methanobacteria* | 0.0362 | 0.000174 | 0.005728 | 0.043009 | 0.004738 | 0.023296 | 0.121371 |
| *Actinobacteria* | 0.001418 | 0.011558 | 0.00309 | 0.002452 | 0.001084 | 0.000774 | 0.024919 |
| *Coriobacteriia* | 0.009837 | 0.03958 | 0.016771 | 0.017958 | 0.006427 | 0.010745 | 0.017251 |
| *Bacteroidia* | 0.0333 | 0.001174 | 0.277208 | 0.188729 | 0.206208 | 0.265022 | 0.04493 |
| *Bacilli* | 0.317793 | 0.280964 | 0.2503 | 0.122857 | 0.016721 | 0.165048 | 0.017103 |
| *Clostridia* | 0.547623 | 0.304067 | 0.390095 | 0.512869 | 0.560144 | 0.431617 | 0.24175 |
| *Erysipelotrichi* | 0.000314 | 0.000953 | 0.000256 | 0.002716 | 0.000138 | 0.000258 | 0.001223 |
| *Betaproteobacteria* | 0.020508 | 0.351972 | 0.024939 | 0.008781 | 0.198751 | 0.001977 | 0.000347 |
| *Deltaproteobacteria* | 0 | 2.33E−05 | 5.91E−05 | 5.27E−05 | 1.06E−05 | 8.60E−05 | 0.00038 |
| *Gammaproteobacteria* | 0.031568 | 0.00929 | 0.027597 | 0.09393 | 0.002326 | 0.093183 | 0.216881 |
| *Mollicutes* | 1.08E−05 | 0 | 0.000138 | 0 | 0.002337 | 0 | 0.000595 |
| *Verrucomicrobiae* | 0.001429 | 0.000244 | 0.003819 | 0.006645 | 0.001115 | 0.007994 | 0.313251 |

TABLE 5

Order distribution in the different bottles, each grown in different conditions. The numbers represent the % of a specific phylum in the bacterial population of the bottle.

| Order | bottle.2 | bottle.3 | bottle.4 | bottle.6 | bottle.7 | bottle.8 | Original feces |
|---|---|---|---|---|---|---|---|
| *Methanobacteriales* | 0.0362 | 0.000174 | 0.005728 | 0.043009 | 0.004738 | 0.023296 | 0.121371 |
| *Bifidobacteriales* | 0.001418 | 0.011558 | 0.00309 | 0.002452 | 0.001084 | 0.000774 | 0.024919 |
| *Coriobacteriales* | 0.009837 | 0.03958 | 0.016771 | 0.017958 | 0.006427 | 0.010745 | 0.017251 |
| *Bacteroidales* | 0.0333 | 0.001174 | 0.277208 | 0.188729 | 0.206208 | 0.265022 | 0.04493 |
| *Bacillales* | 0.197072 | 0.013709 | 1.97E−05 | 2.64E−05 | 0 | 8.60E−05 | 0 |
| *Lactobacillales* | 0.120689 | 0.267209 | 0.250162 | 0.12262 | 0.016721 | 0.16479 | 0.01659 |
| *Turicibacterales* | 3.25E−05 | 4.65E−05 | 0.000118 | 0.000211 | 0 | 0.000172 | 0.000512 |
| *Clostridiales* | 0.547623 | 0.304067 | 0.390095 | 0.512869 | 0.560144 | 0.431617 | 0.24175 |
| *Erysipelotrichales* | 0.000314 | 0.000953 | 0.000256 | 0.002716 | 0.000138 | 0.000258 | 0.001223 |
| *Burkholderiales* | 0.020508 | 0.351972 | 0.024939 | 0.008781 | 0.198751 | 0.001977 | 0.000347 |
| *Desulfovibrionales* | 0 | 2.33E−05 | 5.91E−05 | 5.27E−05 | 1.06E−05 | 8.60E−05 | 0.00038 |
| *Enterobacteriales* | 0.031568 | 0.00929 | 0.027597 | 0.09393 | 0.002326 | 0.093183 | 0.216881 |
| *Anaeroplasmatales* | 1.08E−05 | 0 | 0.000138 | 0 | 0.002337 | 0 | 0.000595 |
| *Verrucomicrobiales* | 0.001429 | 0.000244 | 0.003819 | 0.006645 | 0.001115 | 0.007994 | 0.313251 |

TABLE 6

Family distribution in the different bottles, each grown in different conditions. The numbers represent the % of a specific phylum in the bacterial population of the bottle.

| Family | bottle.2 | bottle.3 | bottle.4 | bottle.6 | bottle.7 | bottle.8 | Original feces |
|---|---|---|---|---|---|---|---|
| *Methanobacteriaceae* | 0.0362 | 0.000174 | 0.005728 | 0.043009 | 0.004738 | 0.023296 | 0.121371 |
| *Bifidobacteriaceae* | 0.001418 | 0.011558 | 0.00309 | 0.002452 | 0.001084 | 0.000774 | 0.024919 |
| *Coriobacteriaceae* | 0.009837 | 0.03958 | 0.016771 | 0.017958 | 0.006427 | 0.010745 | 0.017251 |
| Unidentified | 9.74E−05 | 4.65E−05 | 0.010039 | 7.91E−05 | 0.004908 | 0.000172 | 0.001471 |
| *Bacteroidaceae* | 4.33E−05 | 0.000674 | 0.001181 | 0.003191 | 0.004154 | 0.000774 | 0.011716 |
| *Porphyromonadaceae* | 1.08E−05 | 8.14E−05 | 0.000197 | 7.91E−05 | 0.001806 | 0 | 0.001471 |
| *Prevotellaceae* | 0.021157 | 0.00014 | 0.169773 | 0.161094 | 0.155429 | 0.207427 | 0.024472 |
| *Rikenellaceae* | 7.58E−05 | 3.49E−05 | 0.002303 | 0.000343 | 0.000892 | 8.60E−05 | 0.002495 |
| S24-7 | 0.000433 | 0.000186 | 0.042045 | 0.000316 | 0.016339 | 0.000516 | 0.002644 |
| *Paraprevotellaceae* | 0.011482 | 1.16E−05 | 0.05167 | 0.023627 | 0.022681 | 0.056047 | 0.000661 |
| *Bacillaceae* | 0.197072 | 0.013709 | 1.97E−05 | 2.64E−05 | 0 | 8.60E−05 | 0 |
| Other | 1.08E−05 | 0 | 7.87E−05 | 0 | 0 | 0 | 0 |
| Unidentified | 0.000325 | 0.000721 | 0.000413 | 0.000554 | 0.00034 | 0.000344 | 0.000132 |
| *Enterococcaceae* | 0.003842 | 0.001081 | 0.009133 | 0.00944 | 0.000531 | 0.026648 | 0.009237 |
| *Lactobacillaceae* | 0.113741 | 0.263325 | 0.238332 | 0.109251 | 0.015255 | 0.136164 | 0.000611 |
| *Leuconostocaceae* | 0.002651 | 0.001977 | 0.002086 | 0.003112 | 0.000478 | 0.001375 | 0.001867 |
| *Streptococcaceae* | 0.000119 | 0.000105 | 0.000118 | 0.000264 | 0.000117 | 0.000258 | 0.004742 |
| *Turicibacteraceae* | 3.25E−05 | 4.65E−05 | 0.000118 | 0.000211 | 0 | 0.000172 | 0.000512 |
| Other | 0.002781 | 3.49E−05 | 0.007421 | 0.000369 | 0.00528 | 0.000344 | 0.001917 |
| Unidentified | 0.002706 | 0.001512 | 0.081334 | 0.005116 | 0.066098 | 0.003009 | 0.037725 |
| *Caldicoprobacteraceae* | 0.022185 | 0.006023 | 0 | 0 | 0 | 0 | 0 |
| *Christensenellaceae* | 0.000703 | 0.000419 | 0 | 2.64E−05 | 0 | 0 | 0.000116 |
| *Clostridiaceae* | 0.000649 | 0.032498 | 0.019034 | 0.014477 | 0.018973 | 0.007909 | 0.006147 |
| *Dehalobacteriaceae* | 6.49E−05 | 0.001605 | 0 | 0 | 0 | 0 | 4.96E−05 |
| EtOH8 | 0.000509 | 0.00014 | 0 | 0 | 0 | 0 | 0 |
| *Eubacteriaceae* | 0.001407 | 0.001267 | 0.000138 | 0.01329 | 0.000127 | 0.011261 | 9.91E−05 |
| *Lachnospiraceae* | 0.020919 | 0.019406 | 0.038325 | 0.035652 | 0.048538 | 0.025531 | 0.071897 |
| *Ruminococcaceae* | 0.014675 | 0.019232 | 0.008936 | 0.047888 | 0.016519 | 0.030431 | 0.093395 |
| *Veillonellaceae* | 0.374771 | 0.197189 | 0.234888 | 0.39605 | 0.404608 | 0.353133 | 0.030405 |
| *Mogibacteriaceae* | 0.02646 | 0.000209 | 1.97E−05 | 0 | 0 | 0 | 0 |
| *Tissierellaceae* | 0.079792 | 0.024534 | 0 | 0 | 0 | 0 | 0 |
| *Erysipelotrichaceae* | 0.000314 | 0.000953 | 0.000256 | 0.002716 | 0.000138 | 0.000258 | 0.001223 |
| *Alcaligenaceae* | 0.020497 | 0.002663 | 0.0249 | 0.008781 | 8.50E−05 | 0.001977 | 0.000347 |
| *Comamonadaceae* | 1.08E−05 | 0.349309 | 3.94E−05 | 0 | 0.198666 | 0 | 0 |
| *Desulfovibrionaceae* | 0 | 2.33E−05 | 5.91E−05 | 5.27E−05 | 1.06E−05 | 8.60E−05 | 0.00038 |
| *Enterobacteriaceae* | 0.031568 | 0.00929 | 0.027597 | 0.09393 | 0.002326 | 0.093183 | 0.216881 |
| *Anaeroplasmataceae* | 1.08E−05 | 0 | 0.000138 | 0 | 0.002337 | 0 | 0.000595 |
| *Verrucomicrobiaceae* | 0.001429 | 0.000244 | 0.003819 | 0.006645 | 0.001115 | 0.007994 | 0.313251 |

TABLE 7

Genera distribution in the different bottles, each grown in different conditions. The numbers represent the % of a specific phylum in the bacterial population of the bottle.

| Genera | bottle.2 | bottle.3 | bottle.4 | bottle.6 | bottle.7 | bottle.8 | Original feces |
|---|---|---|---|---|---|---|---|
| *Methanobrevibacter* | 0.0362 | 0.000174 | 0.005728 | 0.043009 | 0.004738 | 0.023296 | 0.121371 |
| *Bifidobacterium* | 0.001418 | 0.011558 | 0.00309 | 0.002452 | 0.001084 | 0.000774 | 0.024919 |
| Unidentified | 0.005855 | 0.009651 | 0.003523 | 0.008386 | 0.003134 | 0.003696 | 0.005883 |
| *Adlercreutzia* | 1.08E−05 | 3.49E−05 | 0.000374 | 0.000211 | 5.31E−05 | 0 | 0.001471 |
| *Collinsella* | 0.002857 | 0.020429 | 0.007854 | 0.007647 | 0.001105 | 0.006447 | 0.008345 |
| *Eggerthella* | 8.66E−05 | 0.000977 | 7.87E−05 | 2.64E−05 | 0 | 0.000172 | 0.000215 |
| *Slackia* | 0.001028 | 0.008488 | 0.004941 | 0.001688 | 0.002135 | 0.00043 | 0.001338 |
| Unidentified | 9.74E−05 | 4.65E−05 | 0.010039 | 7.91E−05 | 0.004908 | 0.000172 | 0.001471 |
| *Bacteroides* | 4.33E−05 | 0.000674 | 0.001181 | 0.003191 | 0.004154 | 0.000774 | 0.011716 |
| *Parabacteroides* | 1.08E−05 | 8.14E−05 | 0.000197 | 7.91E−05 | 0.001806 | 0 | 0.001471 |
| *Prevotella* | 0.021157 | 0.00014 | 0.169773 | 0.161094 | 0.155429 | 0.207427 | 0.024472 |
| Unidentified | 7.58E−05 | 3.49E−05 | 0.002303 | 0.000343 | 0.000892 | 8.60E−05 | 0.002495 |
| Unidentified | 0.000433 | 0.000186 | 0.042045 | 0.000316 | 0.016339 | 0.000516 | 0.002644 |
| Unidentified | 0.011482 | 1.16E−05 | 0.05167 | 0.023627 | 0.022681 | 0.056047 | 0.000661 |
| Unidentified | 0.000563 | 8.14E−05 | 0 | 0 | 0 | 0 | 0 |
| *Bacillus* | 0.196509 | 0.013627 | 1.97E−05 | 2.64E−05 | 0 | 8.60E−05 | 0 |
| Other | 1.08E−05 | 0 | 7.87E−05 | 0 | 0 | 0 | 0 |
| Unidentified | 0.000325 | 0.000721 | 0.000413 | 0.000554 | 0.00034 | 0.000344 | 0.000132 |
| Unidentified | 4.33E−05 | 3.49E−05 | 1.97E−05 | 5.27E−05 | 0 | 0.000172 | 3.30E−05 |
| *Enterococcus* | 0.003799 | 0.001046 | 0.009114 | 0.009383 | 0.000531 | 0.026476 | 0.009204 |
| Unidentified | 0.000909 | 0.000953 | 0.000965 | 0.000264 | 2.12E−05 | 0 | 0 |
| *Lactobacillus* | 0.092962 | 0.255128 | 0.215027 | 0.072913 | 0.011781 | 0.115533 | 0.000595 |
| *Pediococcus* | 0.019869 | 0.007244 | 0.022341 | 0.036074 | 0.003453 | 0.020631 | 1.65E−05 |
| Unidentified | 0.002651 | 0.001977 | 0.002086 | 0.003112 | 0.000478 | 0.001375 | 0.001867 |

TABLE 7-continued

Genera distribution in the different bottles, each grown in different conditions. The numbers represent the % of a specific phylum in the bacterial population of the bottle.

| Genera | bottle.2 | bottle.3 | bottle.4 | bottle.6 | bottle.7 | bottle.8 | Original feces |
|---|---|---|---|---|---|---|---|
| *Lactococcus* | 3.25E−05 | 1.16E−05 | 5.91E−05 | 0.000158 | 3.19E−05 | 0.000172 | 0.000479 |
| *Streptococcus* | 8.66E−05 | 9.30E−05 | 5.91E−05 | 0.000105 | 8.50E−05 | 8.60E−05 | 0.004263 |
| *Turicibacter* | 3.25E−05 | 4.65E−05 | 0.000118 | 0.000211 | 0 | 0.000172 | 0.000512 |
| Other | 0.002781 | 3.49E−05 | 0.007421 | 0.000369 | 0.00528 | 0.000344 | 0.001917 |
| Unidentified | 0.002706 | 0.001512 | 0.081334 | 0.005116 | 0.066098 | 0.003009 | 0.037725 |
| *Caldicoprobacter* | 0.022185 | 0.006023 | 0 | 0 | 0 | 0 | 0 |
| Unidentified | 0.000703 | 0.000419 | 0 | 2.64E−05 | 0 | 0 | 0.000116 |
| Unidentified | 0.000325 | 0.002849 | 0.001831 | 0.000607 | 0.000393 | 8.60E−05 | 0.006147 |
| *Clostridium* | 0.000325 | 0.02965 | 0.017204 | 0.013871 | 0.01858 | 0.007823 | 0 |
| Dehalobacterium | 6.49E−05 | 0.001605 | 0 | 0 | 0 | 0 | 4.96E−05 |
| Unidentified | 0.000509 | 0.00014 | 0 | 0 | 0 | 0 | 0 |
| *Anaerofustis* | 1.08E−05 | 0.000884 | 0 | 0 | 0 | 0 | 0 |
| *Eubacterium* | 0.001396 | 0.000384 | 0.000138 | 0.01329 | 0.000127 | 0.011261 | 9.91E−05 |
| Other | 0.000184 | 1.16E−05 | 0.000177 | 0.002268 | 0.000744 | 0.000344 | 0.002066 |
| Unidentified | 0.003582 | 0.014092 | 0.028483 | 0.004457 | 0.018814 | 0.008424 | 0.018111 |
| *Blautia* | 0.001742 | 0.000337 | 0.000118 | 0.004114 | 0.001848 | 0.001805 | 0.032272 |
| *Coprococcus* | 0.000693 | 2.33E−05 | 0.000354 | 0.004246 | 0.002826 | 0.005931 | 0.00266 |
| *Dorea* | 0.000444 | 3.49E−05 | 0.000531 | 0.000448 | 0.001519 | 0.00043 | 0.003867 |
| *Lachnospira* | 0.009091 | 0.00479 | 0 | 0.007278 | 3.19E−05 | 0.000516 | 0.000512 |
| *Roseburia* | 0.000108 | 0 | 0.00187 | 0.007937 | 0 | 0.004212 | 0.000578 |
| *Ruminococcus* | 0.005076 | 0.000116 | 0.006791 | 0.004905 | 0.022755 | 0.003868 | 0.011831 |
| Unidentified | 0.011591 | 0.003291 | 0.004842 | 0.033094 | 0.012727 | 0.022436 | 0.046565 |
| *Faecalibacterium* | 0.00118 | 0.000221 | 0.000905 | 0.002769 | 0.002072 | 0.003009 | 0.01659 |
| *Oscillospira* | 0.001439 | 0.009314 | 0.002244 | 0.011365 | 0.001562 | 0.000602 | 0.000446 |
| *Ruminococcus* | 0.000465 | 0.006407 | 0.000945 | 0.000659 | 0.000159 | 0.004384 | 0.029793 |
| *Acidaminococcus* | 0.348235 | 0.185154 | 0.181111 | 0.263014 | 0.312749 | 0.275423 | 0.000711 |
| *Dialister* | 0.024415 | 0.008325 | 0.044131 | 0.122805 | 0.091158 | 0.061377 | 0.001223 |
| *Phascolarctobacterium* | 0.002121 | 0.003639 | 0.009566 | 0.010073 | 0.000701 | 0.016333 | 0.028009 |
| *Veillonella* | 0 | 6.98E−05 | 7.87E−05 | 0.000158 | 0 | 0 | 0.000463 |
| Unidentified | 0.02646 | 0.000209 | 1.97E−05 | 0 | 0 | 0 | 0 |
| *Sporanaerobacter* | 0.011266 | 0.005918 | 0 | 0 | 0 | 0 | 0 |
| *Tepidimicrobium* | 0.05766 | 0.018615 | 0 | 0 | 0 | 0 | 0 |
| *Soehngenia* | 0.010865 | 0 | 0 | 0 | 0 | 0 | 0 |
| Unidentified | 0 | 0.000919 | 0 | 2.64E−05 | 1.06E−05 | 0 | 4.96E−05 |
| *Catenibacterium* | 0.000303 | 3.49E−05 | 0.000256 | 0.002532 | 0.000127 | 0.000258 | 0.000694 |
| *Eubacterium* | 1.08E−05 | 0 | 0 | 0.000158 | 0 | 0 | 0.000479 |
| *Sutterella* | 0.020497 | 0.002663 | 0.0249 | 0.008781 | 8.50E−05 | 0.001977 | 0.000347 |
| Unidentified | 1.08E−05 | 0.349309 | 3.94E−05 | 0 | 0.198666 | 0 | 0 |
| *Desulfovibrio* | 0 | 2.33E−05 | 5.91E−05 | 5.27E−05 | 1.06E−05 | 8.60E−05 | 0.00038 |
| Unidentified | 0.031005 | 0.008883 | 0.02679 | 0.091055 | 0.002018 | 0.09155 | 0.203199 |
| *Citrobacter* | 0.000563 | 0.000407 | 0.000807 | 0.002874 | 0.000308 | 0.001633 | 0.013682 |
| *Anaeroplasma* | 1.08E−05 | 0 | 0.000138 | 0 | 0.002337 | 0 | 0.000595 |
| *Akkermansia* | 0.001429 | 0.000244 | 0.003819 | 0.006645 | 0.001115 | 0.007994 | 0.313251 |

TABLE 8 representative example of microorganism genera and phylum typically found in a human fecal sample.

| Genera | Phylum |
|---|---|
| *Actinomyces* | Actinobacteria |
| *Adlercreutzia* | Actinobacteria |
| *Atopobium* | Actinobacteria |
| *Bifidobacterium* | Actinobacteria |
| *Collinsella* | Actinobacteria |
| *Corynebacterium* | Actinobacteria |
| *Dermabacter* | Actinobacteria |
| *Eggerthella* | Actinobacteria |
| *Gardnerella* | Actinobacteria |
| *Gordonibacter* | Actinobacteria |
| *Kocuria* | Actinobacteria |
| *Leifsonia* | Actinobacteria |
| *Micrococcus* | Actinobacteria |
| *Mobiluncus* | Actinobacteria |
| *Mycobacterium* | Actinobacteria |
| *Propionibacterium* | Actinobacteria |
| *Rothia* | Actinobacteria |
| *Slackia* | Actinobacteria |
| *Streptomyces* | Actinobacteria |
| *Varibaculum* | Actinobacteria |
| *Methanobrevibacter* | Archea |
| *Methanosphaera* | Archea |
| *Alistipes* | Bacteroidetes |
| *Bacteroides* | Bacteroidetes |
| *Barnesiella* | Bacteroidetes |
| *Capnocytophaga* | Bacteroidetes |
| *Dysgonomonas* | Bacteroidetes |
| *Odoribacter* | Bacteroidetes |
| *Parabacteroides* | Bacteroidetes |
| *Paraprevotella* | Bacteroidetes |
| *Porphyromonas* | Bacteroidetes |
| *Prevotella* | Bacteroidetes |
| *Tannerella* | Bacteroidetes |
| *Deinococcus* | Deinococcus-Thermus |
| *Acetanaerobacterium* | Firmicutes |
| *Acidaminococcus* | Firmicutes |
| *Anaerococcus* | Firmicutes |
| *Anaerostipes* | Firmicutes |
| *Anaerotruncus* | Firmicutes |
| *Anaerovorax* | Firmicutes |

TABLE 8-continued representative example of microorganism genera and
phylum typically found in a human fecal sample.

| Genera | Phylum |
| --- | --- |
| Bacillus | Firmicutes |
| Blautia | Firmicutes |
| Butyricicoccus | Firmicutes |
| Butyrivibrio | Firmicutes |
| Catabacter | Firmicutes |
| Catenibacterium | Firmicutes |
| Catonella | Firmicutes |
| Christensenella | Firmicutes |
| Clostridium | Firmicutes |
| Coprobacillus | Firmicutes |
| Coprococcus | Firmicutes |
| Desulfitobacterium | Firmicutes |
| Dialister | Firmicutes |
| Dorea | Firmicutes |
| Enterococcus | Firmicutes |
| Erysipelotrichaceae | Firmicutes |
| Eubacterium | Firmicutes |
| Exiguobacterium | Firmicutes |
| Faecalibacterium | Firmicutes |
| Finegoldia | Firmicutes |
| Flavonifractor | Firmicutes |
| Gemella | Firmicutes |
| Gramilicatella | Firmicutes |
| Lachnospiraceae | Firmicutes |
| Lactobacillus | Firmicutes |
| Lactococcus | Firmicutes |
| Leuconostoc | Firmicutes |
| Listeria | Firmicutes |
| Marvinbryantia | Firmicutes |
| Megamonas | Firmicutes |
| Megasphaera | Firmicutes |
| Oenococcus | Firmicutes |
| Oribacterium | Firmicutes |
| Oscillibacter | Firmicutes |
| Paenibacillus | Firmicutes |
| Paenisporosarcina | Firmicutes |
| Pediococcus | Firmicutes |
| Peptococcus | Firmicutes |
| Peptoniphilus | Firmicutes |
| Peptostreptococcus | Firmicutes |
| Phascolarctobacterium | Firmicutes |
| Roseburia | Firmicutes |
| Ruminococcus | Firmicutes |
| Selenomonas | Firmicutes |
| Solobacterium | Firmicutes |
| Staphylococcus | Firmicutes |
| Streptococcus | Firmicutes |
| Subdoligranulum | Firmicutes |
| Turicibacter | Firmicutes |
| Ureaplasma | Firmicutes |
| Veillonella | Firmicutes |
| Weissella | Firmicutes |
| Cetobacterium | Fusobacteria |
| Fusobacterium | Fusobacteria |
| Leptotrichia | Fusobacteria |
| Victivallis | Lentisphaerae |
| Achromobacter | Proteobacteria |
| Acinetobacter | Proteobacteria |
| Aeromonas | Proteobacteria |
| Aggregatibacter | Proteobacteria |
| Arcobacter | Proteobacteria |
| Bartonella | Proteobacteria |
| Bilophila | Proteobacteria |
| Bradyrhizobium | Proteobacteria |
| Brevundimonas | Proteobacteria |
| Burkholderiales | Proteobacteria |
| Campylobacter | Proteobacteria |
| Cardiobacterium | Proteobacteria |
| Cedecea | Proteobacteria |
| Citrobacter | Proteobacteria |
| Desulfovibrio | Proteobacteria |
| Edwardsiella | Proteobacteria |
| Eikenella | Proteobacteria |
| Enhydrobacter | Proteobacteria |
| Enterobacter | Proteobacteria |
| Escherichia | Proteobacteria |
| Geobacter | Proteobacteria |
| Grimontia | Proteobacteria |
| Haemophilus | Proteobacteria |
| Hafnia | Proteobacteria |
| Helicobacter | Proteobacteria |
| Kingella | Proteobacteria |
| Klebsiella | Proteobacteria |
| Kluyvera | Proteobacteria |
| Laribacter | Proteobacteria |
| Lautropia | Proteobacteria |
| Methylobacterium | Proteobacteria |
| Moraxella | Proteobacteria |
| Morganella | Proteobacteria |
| Neisseria | Proteobacteria |
| Nitrobacter | Proteobacteria |
| Oxalobacter | Proteobacteria |
| Parasutterella | Proteobacteria |
| Pelomonas | Proteobacteria |
| Plesiomonas | Proteobacteria |
| Proteus | Proteobacteria |
| Providencia | Proteobacteria |
| Pseudomonas | Proteobacteria |
| Ralstonia | Proteobacteria |
| Raoultella | Proteobacteria |
| Rhizobium | Proteobacteria |
| Salmonella | Proteobacteria |
| Shewanella | Proteobacteria |
| Shigella | Proteobacteria |
| Simonsiella | Proteobacteria |
| Sphingomonas | Proteobacteria |
| Stenotrophomonas | Proteobacteria |
| Succinatimonas | Proteobacteria |
| Sutterella | Proteobacteria |
| Vibrio | Proteobacteria |
| Xenorhabdus | Proteobacteria |
| Yersinia | Proteobacteria |
| Yokenella | Proteobacteria |
| Anaerobaculum | Synergistetes |
| Pyramidobacter | Synergistetes |
| Synergistes | Synergistetes |
| Anaeroplasma | Tenericutes |
| Holdemania | Tenericutes |
| Mycoplasma | Tenericutes |
| Akkermansia | Verrucomicrobia |
| Anaerofustis | Firmicutes |
| Aneurinibacillus | Firmicutes |
| Bryantella | Firmicutes |
| Dehalobacterium | Firmicutes |
| Mitsuokella | Firmicutes |
| Mogibacterium | Firmicutes |
| Parvimonas | Firmicutes |
| Planobacterium | Bacteroidetes |
| Pseudoflavonifractor | Firmicutes |

Example 2

Biofilm Growth on Particles Using Soil as an Origin Microbiota

A fresh soil sample was obtained and mixed. A small portion was sent to sequencing (original sample). The rest was mixed in PBSX1 and 25 ml was transferred to sample tubes that contain 2 gr of sterile matrix including: pomegranate, passion fruit, DCP and MCC particles. The tubes were grown as a biofilm in PBSX1 with overnight shaking at 100 rpm. After 1 day of incubation, a portion of the sample was sequenced (Soil biofilm 1—B1). The remaining's were incubated with 4 different synthetic growth media (one in each tube) including: brain-heart infusion medium (BHI), LB, ¼ LB and *Brucella* broth. The tubes were grown as a biofilm for 4 days that include 2 hours of shaking at 100 rpm while at the rest of the time, the tubes were in static conditions. The growth media was replaced on a daily basis. The biofilms from all of tubes were recombined and sequenced (Soil biofilm 5—B5).

As a control, the soil bacteria were grown in tubes under planktonic growth conditions without the matrix. The tubes with the soil bacteria were placed in PBSX1 for overnight shaking at 230 rpm. After 1 day of incubation, a small amount of the liquid was sequenced (Soil planktonic 1—P1). The rest was centrifuged and the bacterial pellet was divided into 4 different synthetic growth media including BHI, LB, ¼ LB and *Brucella* broth. The tubes were grown in planktonic conditions for 4 more days with constant shaking at 230 rpm. The growth media was replaced on a daily basis. The biofilms from all of tubes were recombined and sequenced (Soil planktonic 5—P5).

Results

Figure 3:
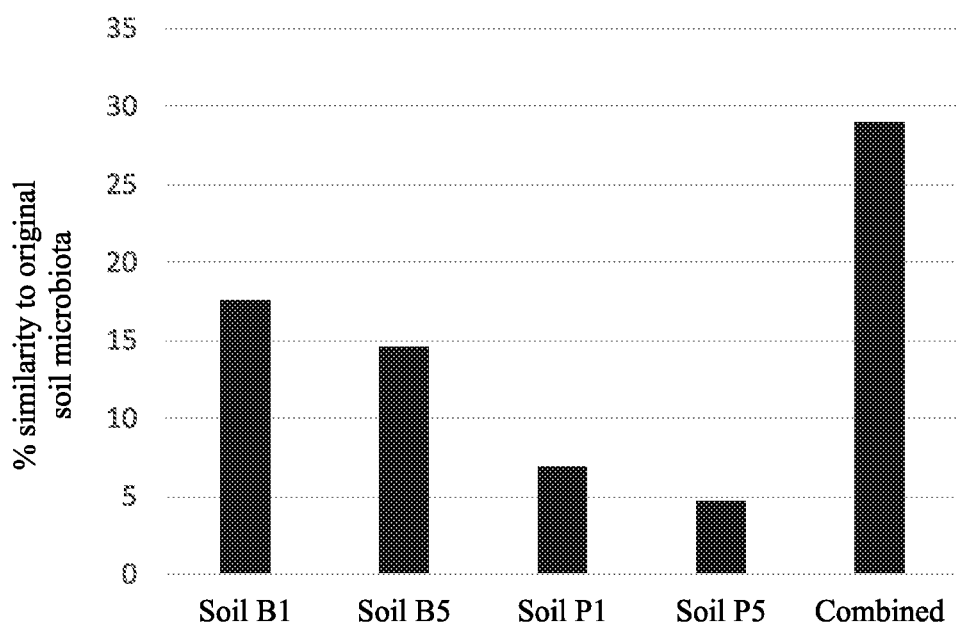
FIG. 3 is a bar graph that demonstrates the similarity percentage of different samples compared to the original soil microbiota.

Sequence analysis results are presented in Table 9 and FIG. 3. The original soil microbiota included 154 bacterial families. 43 bacterial families were identified in the B1 biofilm sample, thus 28% similarity to the origin microbiota. The corresponding planktonic sample (P1) contained 25 bacterial families, thus 16% similarity to the origin microbiota.

Soil bacteria are generally divided into three states: active, dormant and non-viable. According to the art, the active bacteria in soil varies from about 0.1 to about 50% under ideal conditions. Thus, assuming the sample has 50% active cells, the adjusted rate of similarity ranges to about 56%.

TABLE 9

| Bacterial families | Original soil microbiota | Soil B1 | Soil B5 | Planktonic P1 | Planktonic P5 |
| --- | --- | --- | --- | --- | --- |
| Unknown (order-MND1) | + | − | − | − | − |
| [Amoebophilaceae] | + | − | − | − | − |
| [Chthoniobacteraceae] | + | − | + | + | − |
| [Entotheonellaceae] | + | − | − | − | − |
| [Fimbriimonadaceae] | + | + | − | − | − |
| [Kouleothrixaceae] | + | − | − | − | − |
| [Thermobaculaceae] | + | − | − | − | − |
| [Weeksellaceae] | + | − | − | − | − |
| 01D2Z36 | + | − | − | − | − |
| 0319-6A21 | + | − | − | − | − |
| 5B-12 | + | − | − | − | − |
| A4b | + | + | − | − | − |
| Acetobacteraceae | + | − | − | − | − |
| Actinosynnemataceae | + | − | − | − | − |
| AK1AB1_02E | + | − | − | − | − |
| AKIW874 | + | − | − | − | − |
| Alcaligenaceae | + | + | + | − | − |
| Alicyclobacillaceae | + | − | − | − | − |
| Alteromonadaceae | + | + | − | − | − |
| Anaeroplasmataceae | + | − | − | − | − |
| Ardenscatenaceae | + | + | − | − | − |
| Armatimonadaceae | + | − | − | − | − |
| Aurantimonadaceae | + | − | − | − | − |
| Bacillaceae | + | + | + | + | + |
| Bacteriovoracaceae | + | − | − | − | − |
| Bdellovibrionaceae | + | − | − | − | − |
| Beijerinckiaceae | + | − | − | − | − |
| Beutenbergiaceae | + | − | − | − | − |
| Bogoriellaceae | + | − | − | − | − |
| Bradyrhizobiaceae | + | + | − | − | − |
| Burkholderiaceae | + | − | − | − | − |
| C111 | + | + | − | − | − |
| Caldilineaceae | + | − | − | − | − |
| Caulobacteraceae | + | + | − | − | − |
| Cellulomonadaceae | + | − | − | + | − |
| Chitinophagaceae | + | + | + | + | − |

TABLE 9-continued

| Bacterial families | Original soil microbiota | Soil B1 | Soil B5 | Planktonic P1 | Planktonic P5 |
| --- | --- | --- | --- | --- | --- |
| Chloroflexaceae | + | − | − | − | − |
| Clostridiaceae | + | + | + | + | + |
| Comamonadaceae | + | + | + | + | − |
| Conexibacteraceae | + | + | + | − | − |
| Corynebacteriaceae | + | − | − | − | − |
| Coxiellaceae | + | − | − | − | − |
| Coxiellaceae | + | − | − | − | − |
| Cryomorphaceae | + | − | − | − | − |
| Cryptosporangiaceae | + | − | − | − | − |
| Cyclobacteriaceae | + | − | − | − | − |
| Cystobacteraceae | + | + | − | − | − |
| Cystobacterineae | + | − | − | − | − |
| Cytophagaceae | + | + | + | + | − |
| Deinococcaceae | + | − | − | − | − |
| Dermabacteraceae | + | − | − | − | − |
| Dolo_23 | + | − | − | − | − |
| EB1017 | + | − | − | − | − |
| Ectothiorhodospiraceae | + | − | + | − | − |
| Ellin515 | + | − | − | − | − |
| Ellin517 | + | − | − | − | − |
| Ellin5301 | + | − | − | − | − |
| Ellin6075 | + | − | + | − | − |
| Enterobacteriaceae | + | + | + | + | + |
| Erythrobacteraceae | + | + | − | − | − |
| Euzebyaceae | + | − | − | − | − |
| FFCH4570 | + | − | − | − | − |
| FFCH7168 | + | − | − | − | − |
| Flammeovirgaceae | + | + | − | − | − |
| Flavobacteriaceae | + | + | − | − | − |
| Frankiaceae | + | − | − | − | − |
| Gaiellaceae | + | − | − | − | − |
| Gemmataceae | + | + | − | − | − |
| Gemmatimonadaceae | + | − | − | − | − |
| Geodermatophilaceae | + | + | + | + | − |
| Gordoniaceae | + | − | − | − | − |
| Haliangiaceae | + | − | − | − | − |
| Helicobacteraceae | + | + | − | − | − |
| HTCC2089 | + | − | − | − | − |
| HTCC2188 | + | − | − | − | − |
| Hyphomicrobiaceae | + | + | + | − | − |
| Hyphomonadaceae | + | − | − | − | − |
| Iamiaceae | + | − | − | − | − |
| Intrasporangiaceae | + | − | − | − | − |
| Isosphaeraceae | + | + | − | − | − |
| JdFBGBact | + | − | − | − | − |
| Kineosporiaceae | + | − | − | + | − |
| Lachnospiraceae | + | − | + | + | + |
| Lactobacillaceae | + | − | − | + | − |
| Marinilabiaceae | + | − | − | − | − |
| mb2424 | + | − | + | − | − |
| Methylobacteriaceae | + | − | + | − | − |
| Methylocystaceae | + | − | − | − | − |
| Methylophilaceae | + | + | + | − | − |
| Microbacteriaceae | + | + | − | − | − |
| Micrococcaceae | + | + | + | + | − |
| Micromonosporaceae | + | − | − | − | − |
| Microthrixaceae | + | − | − | − | − |
| MND4 | + | − | − | − | − |
| Moraxellaceae | + | + | + | + | + |
| Mycobacteriaceae | + | − | − | − | − |
| Myxococcaceae | + | − | − | − | − |
| Nakamurellaceae | + | − | − | − | − |
| Nannocystaceae | + | − | + | − | − |
| Nitrosomonadaceae | + | − | − | − | − |
| Nitrospiraceae | + | − | + | − | − |
| Nocardiaceae | + | − | − | − | − |
| Nocardioidaceae | + | + | + | + | − |
| Oceanospirillaceae | + | − | + | − | − |
| OM27 | + | − | − | − | − |
| OM60 | + | + | − | − | − |
| Opitutaceae | + | − | − | − | − |
| Oscillochloridaceae | + | − | − | − | − |
| Oxalobacteraceae | + | + | + | + | + |
| Paenibacillaceae | + | − | + | + | + |
| Parachlamydiaceae | + | − | − | − | − |
| Patulibacteraceae | + | − | − | − | − |

TABLE 9-continued

| Bacterial families | Original soil microbiota | Soil B1 | Soil B5 | Planktonic P1 | Planktonic P5 |
|---|---|---|---|---|---|
| Phyllobacteriaceae | + | − | − | − | − |
| Pirellulaceae | + | + | + | − | − |
| Piscirickettsiaceae | + | + | − | − | − |
| Planctomycetaceae | + | + | − | + | − |
| Planococcaceae | + | + | + | + | + |
| Polyangiaceae | + | − | + | − | − |
| Prevotellaceae | + | − | − | − | − |
| Promicromonosporaceae | + | + | − | − | − |
| Propionibacteriaceae | + | − | − | + | − |
| Pseudomonadaceae | + | + | + | + | + |
| Pseudonocardiaceae | + | − | + | − | − |
| RB40 | + | − | − | − | − |
| Rhizobiaceae | + | − | − | + | − |
| Rhodobacteraceae | + | + | + | − | − |
| Rhodobiaceae | + | − | − | − | − |
| Rhodocyclaceae | + | − | − | − | − |
| Rhodospirillaceae | + | − | − | − | − |
| Rhodothermaceae | + | − | − | − | − |
| Rickettsiaceae | + | − | − | − | − |
| Rubrobacteraceae | + | − | + | − | − |
| S47 | + | − | − | − | − |
| Saprospiraceae | + | + | − | − | − |
| Sinobacteraceae | + | − | − | − | − |
| SJA-101 | + | − | − | − | − |
| Solibacteraceae | + | − | − | − | − |
| Solirubrobacteraceae | + | − | − | − | − |
| Sphingobacteriaceae | + | + | − | − | − |
| Sphingomonadaceae | + | + | + | + | − |
| Sporichthyaceae | + | − | + | − | − |
| Staphylococcaceae | + | − | − | − | − |
| Streptomycetaceae | + | + | + | − | − |
| Streptosporangiaceae | + | − | − | − | − |
| Syntrophobacteraceae | + | − | − | + | − |
| Thermoactinomycetaceae | + | − | − | − | − |
| Thermomonosporaceae | + | − | − | − | − |
| Trueperaceae | + | − | − | − | − |
| UD5 | + | − | − | − | − |
| Veillonellaceae | + | − | − | − | − |
| Verrucomicrobiaceae | + | − | − | − | − |
| Williamsiaceae | + | − | − | − | − |
| Xanthobacteraceae | + | − | − | − | − |
| Xanthomonadaceae | + | + | + | + | + |

Figure 4:
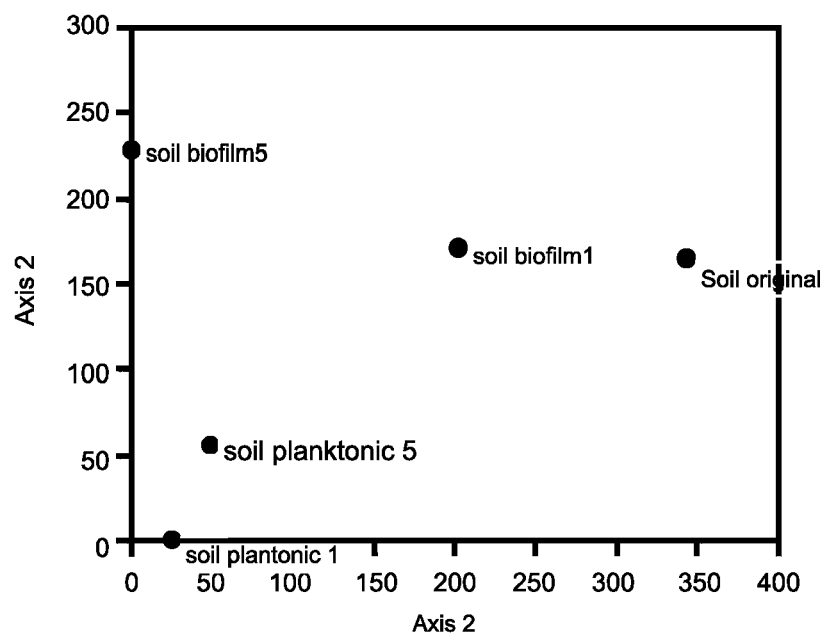
FIG. 4 is a plot showing the bacterial genera by detrended correspondence analysis (DCA) ordination analysis of soil microbiota and human oral microbiota grown in different conditions.

An ordination analysis was done in order to compare the similarity of the bacterial families. Detrended Correspondence Analysis (DCA) is a multivariate ordination model that is specialized for use on ecological data sets with abundance of data. The DCA analysis showed higher abundance and similarity to the original soil microbiota in the matrix grown samples as compared to the planktonic sample as shown in FIG. 4. Similarity comparison between soil original microbiota and other samples based on different similarity or distance indices was done. In Bray-Curtis and Simpson indices, two samples are closer when the index value is close to 1. In Euclidean distance, small index values indicate greater proximity. The results of this analysis are presented in Table 10.

TABLE 10

Similarity/distance indexes obtained from soil data analysis.

| Similarity/distance index | | soil biofilm1 | soil biofilm5 | soil planktonic1 | soil planktonic 5 |
|---|---|---|---|---|---|
| Bray-Curtis | Soil original vs. | 0.27 | 0.02 | 0.02 | 0.05 |
| Simpson | Soil original vs. | 0.72 | 0.46 | 0.56 | 0.69 |

TABLE 10-continued

Similarity/distance indexes obtained from soil data analysis.

| Similarity/distance index | | soil biofilm1 | soil biofilm5 | soil planktonic1 | soil planktonic 5 |
|---|---|---|---|---|---|
| Euclidean | Soil original vs. | 15.6 | 35.8 | 52.2 | 49.5 |

Figure 5:
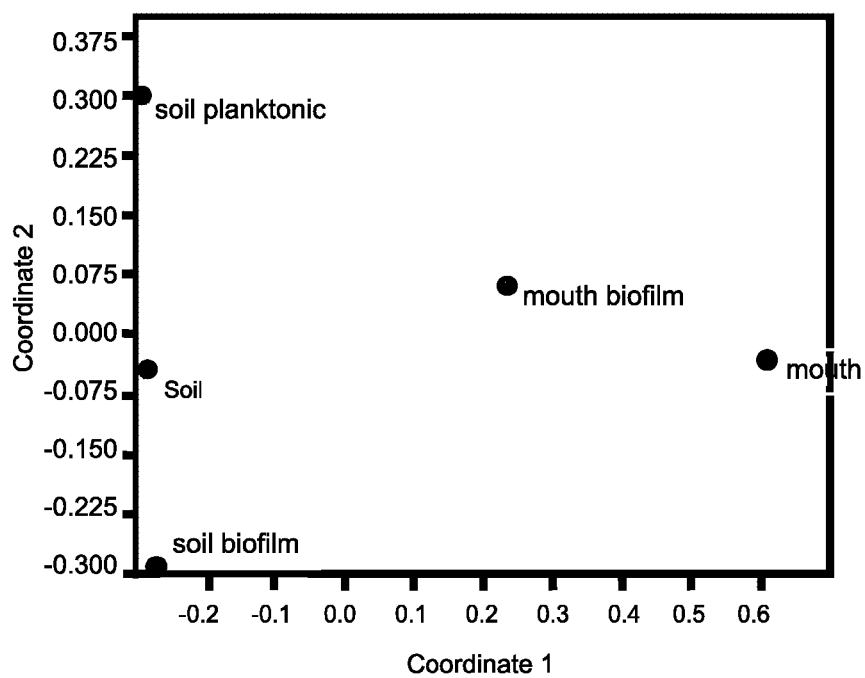
FIG. 5 is a plot showing the results of a multidimensional scaling (MDS) ordination analysis of bacteria populations from soil and human oral microbiota grown in different conditions.

These results are supported by other ordination analysis models such as non-metric multidimensional scaling (MDS), which is based on a distance matrix of the analyzed samples. The MDS analysis can be performed using different similarity indices according to the nature of the data. MDS analysis based on Simpson similarity index which takes into account the number of species present in the sample (OTUs), as well as the relative abundance of each species. This analysis also reveals higher abundance and similarity to the original microbiota in the matrix grown samples as compared to the planktonic sample as shown in FIG. 5.

By combining the matrix grown with the planktonic grown samples it is possible to produce a composition comprising a higher rate of similarity to the source. Combining the bacterial families present in matrix grown with the planktonic grown samples in this experiment yielded a composition comprising 40% similarity to the source.

In some of the soil samples (soil P1, P5 and B5), one genera are substantially more abundant than other genera. For example, in the B5 sample the relative abundance of the *Klebsiella* genus was 38%. Since in a co-culture different strains are competing with each other for resources, decreasing the percent of a certain genera or family may allow a richer diversity. It is optional to use an antibiotic, bacteriophage, competing bacteria or any other method that will reduce a certain population to allow more genera to grow in a sample.

Example 3

Biofilm Growth on Particles Using Human Oral Microbiota as an Origin Microbiota Five swabs from a human mouth were taken, one was immediately sent to sequencing (Original sample) and the other 4 were placed each in a different tube containing 2 gr of sterile matrix of pomegranate, passion fruit, DCP and MCC particles and 4 different growth media (one in each tube) including BHI, LB, ¼ LB and *Brucella* broth. The tubes were placed overnight in shaking conditions at 100 rpm. The next day, the medium was refreshed and the tubes were grown as biofilm for another 4 days. The matrices with the biofilm from all of the samples were then united and sequenced.

Sequence analysis of the mouth swab sample identified 49 bacterial families. Of these, 17 bacterial families were identified in the grown biofilm sample amounting to 35% similarity to the original microbiota as detailed in Table 11.

TABLE 11

Bacterial families identified in biofilm grown culture compared to the original microbiota

| Bacterial families | Oral original microbiota | Oral biofilm grown sample |
|---|---|---|
| [Acidaminobacteraceae] | + | − |
| [Mogibacteriaceae] | + | − |
| [Paraprevotellaceae] | + | + |
| [Tissierellaceae] | + | − |
| [Weeksellaceae] | + | − |
| Actinomycetaceae | + | − |
| Aerococcaceae | + | + |
| Bacillaceae | + | + |
| Bifidobacteriaceae | + | + |
| Bradyrhizobiaceae | + | − |
| Burkholderiaceae | + | − |
| Campylobacteraceae | + | − |
| Cardiobacteriaceae | + | − |
| Carnobacteriaceae | + | + |
| Cellulomonadaceae | + | − |
| Clostridiaceae | + | + |
| Coriobacteriaceae | + | − |
| Corynebacteriaceae | + | − |
| Cytophagaceae | + | − |
| Desulfobacteraceae | + | − |
| Dethiosulfovibrionaceae | + | − |
| Enterobacteriaceae | + | + |
| Enterococcaceae | + | + |
| Erysipelotrichaceae | + | − |
| Flavobacteriaceae | + | − |
| Fusobacteriaceae | + | + |
| Gemellaceae | + | − |
| Hyphomicrobiaceae | + | − |
| Kineosporiaceae | + | − |
| Lachnospiraceae | + | + |
| Lactobacillaceae | + | + |
| Leptotrichiaceae | + | − |
| Micrococcaceae | + | − |
| Mycoplasmataceae | + | − |
| Neisseriaceae | + | − |
| Pasteurellaceae | + | − |
| Peptococcaceae | + | − |
| Peptostreptococcaceae | + | − |
| Planococcaceae | + | + |
| Porphyromonadaceae | + | + |
| Prevotellaceae | + | − |
| Propionibacteriaceae | + | − |
| Pseudomonadaceae | + | + |
| Pseudonocardiaceae | + | − |
| Ruminococcaceae | + | − |
| Spirochaetaceae | + | − |
| Staphylococcaceae | + | + |
| Streptococcaceae | + | + |
| Veillonellaceae | + | + |

Example 4

Biofilm Growth on Particles Using Frozen Samples as an Origin Microbiota

The bacterial communities were obtained from soil microbiota and oral microbiota (examples 2 and 3) and from individual strains or a mix of two known strains in order to examine the possibility for a scale up process.

The viability of bacteria in soil microbiota and oral microbiota samples that were stored at −20° C. for 1 week was checked. This was done by thawing and plating dilutions of 3 µL in different agar media as LB, MRS, RCM, Brucella in duplicates. Plates were incubated at room temperature at aerobic and anaerobic conditions. L. plantarum and B. longum from stocks were plated in MRS and RCM agar plates respectively and were incubated at 37° C. in an anaerobic hood. In the next day, the bacterial growth was checked on plates. Plates were incubated for the weekend in anaerobic and aerobic conditions at room temperature. A few small colonies of L. plantarum and B. longum were added to MRS and RCM broth respectively. L. plantarum was incubated overnight at 37° C. with aerobic conditions and shaking at 180 rpm. B. longum was incubated overnight at 37° C. in anaerobic hood. The next day, optical density (OD) of each strain (L. plantarum and B. longum) was measured and a dilution of each strain to a final OD of 0.1 in new sterile tubes was done, according to Table 12.

TABLE 12

Bacteria and proliferative conditions to a small-scale matrix.

| Microbiota | Sample | DCP/MCC mix | Growth medium | Tube (ml) | Units (Num of tubes) | Proliferative conditions |
|---|---|---|---|---|---|---|
| Soil community biofilm | SM LB | 2 g all grains mx | 25 ml LB | 50 | 2 | 24 h, 30 C., aerobic |
| Soil community biofilm | SM RCM | 2 gr all grains mix | 25 ml RCM | 50 | 2 | 24 h, 30 C., aerobic |
| Soil community biofilm | SM Brucella | 2 gr all grain mix | 25 ml Brucella | 50 | 2 | 24 h, 30 C., aerobic |
| Soil community planktonic | SP LB | 2 g all grain mix | 25 ml LB | 50 | 2 | 24 h, 30 C., aerobic |
| Soil community planktonic | SP RCM | 2 gr all grain mix | 25 ml RCM | 50 | 2 | 24 h, 30 C., aerobic |
| Soil community planktonic | SP Brucella | 2 gr all grain mix | 25 ml Brucella | 50 | 2 | 24 h, 30 C., aerobic |
| Oral community biofilm | MM LB | 2 g all grain mix | 25 ml LB | 50 | 2 | 24 h, 37 C., aerobic |
| Oral community biofilm | MM RCM | 2 gr all grain mix | 25 ml RCM | 50 | 2 | 24 h, 37 C., aerobic |
| Oral community biofilm | MM Brucella | 2 gr all grain mix | 25 ml Brucella | 50 | 2 | 24 h, 37 C., aerobic |
| L. plantarum | L | 2 g | 25 ml MRS | 50 | 7 | 24 h, anaerobic |
| B. longum | B | 2 g | 25 ml RCM | 50 | 7 | 24 h, rt, anaerobic |
| L. plantarum and B. longum | LB1 | 2 g | 25 ml RCM | 50 | 5 | 24 h, rt anaerobic |
| Control | C1 | 2 g all grain mix | 25 ml RCM | 50 | 2 | 24 h, 37 C. aerobic |
| Control | C2 | 2 gr of DCP/MCC | 25 ml RCM | 50 | 2 | 24 h, rt aerobic |

The samples were incubated in shaking at 100 rpm at 30° C. for 2 hours. After 2 hours, the tubes were transferred to their respective proliferative conditions (according to Table 12).

For a culture volume scale up of soil and oral microbiota, one tube of each sample was centrifuged at 500 rpm for two minutes. Supernatant was discarded and 10 ml of PBSX1 were added per tube. The tubes were mixed gently in an incubator at 100 rpm for 1 minute. Each sample was transferred through vacuum filter of 80 µm. The matrix from the three samples was combined and sent to DNA sequencing analysis Another approach for scale up of culture volume was tested by transferring of defrosted matrix particles to a new matrix. One tube of each L. plantarum and B. longum samples were centrifuged at 500 rpm for two minutes. The supernatant was discarded and 10 ml of PBSX1 per tube were added. The tubes were mixed gently in incubator at 100 rpm for 1 minute. Each sample was transferred through vacuum filter of 80 µm. Finally, 1 gr of matrix particles was transferred to the new matrix bottle. Yet another approach for scale up of culture volume was tested by transferring of biofilm detached bacteria of L. plantarum and B. longum samples. One tube of each sample was centrifuged at 500 rpm for two minutes. The supernatant was discarded, the sample was washed once with 10 ml PBSX1 and filtered. 1 ml RCM broth was added, the samples were vortexed 3 times for 30 sec high speed. The supernatant was transferred to the new matrix.

For quantification and acid resistance of L. plantarum and B. longum samples only, the medium of each sample was removed and 10 ml of PBSX1 per tube were added and mixed gently by incubator at 100 rpm for 1 minute. Samples were transferred to vacuum filter of 80 µm and mixed well after filtration. Acid resistance at pH 2 was tested by adding 5 ml of pH 2 solution to each sample. The cells were incubated for 1 hour at room temperature. After incubation, samples were washed once with 5 ml PBSX1 and 1 ml of PBSX1 was added followed by vortex 3 times for 30 sec at high speed. Acid resistance at pH 7 was tested by adding 5 ml of pH 7 solution to each sample. The cells were incubated for 1 hour at room temperature. After incubation, samples were washed once with 5 ml of PBSX1 and 1 ml of PBSX1 was added followed by vortex 3 times for 30 sec at high speed. For long incubation, the remaining tubes (including control tube) were incubated according to the conditions specified in Table 12.

Figure 6:
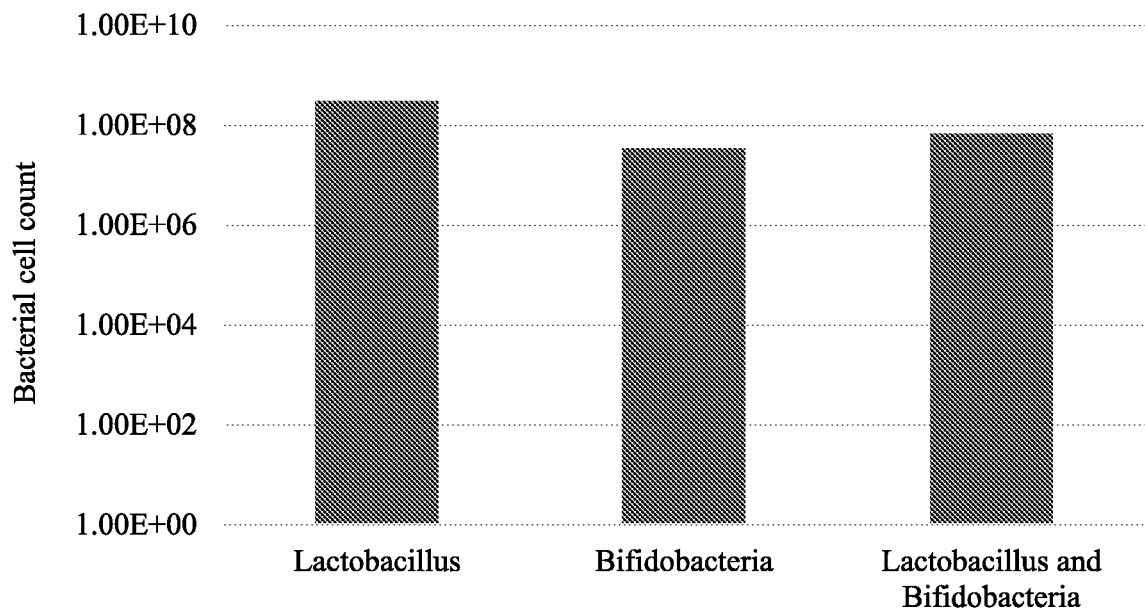
FIG. 6 is a bar graph showing the bacterial growth of *Lactobacillus* and *Bifidobacterium* strains and their mix in a small scale.
Figure 7:
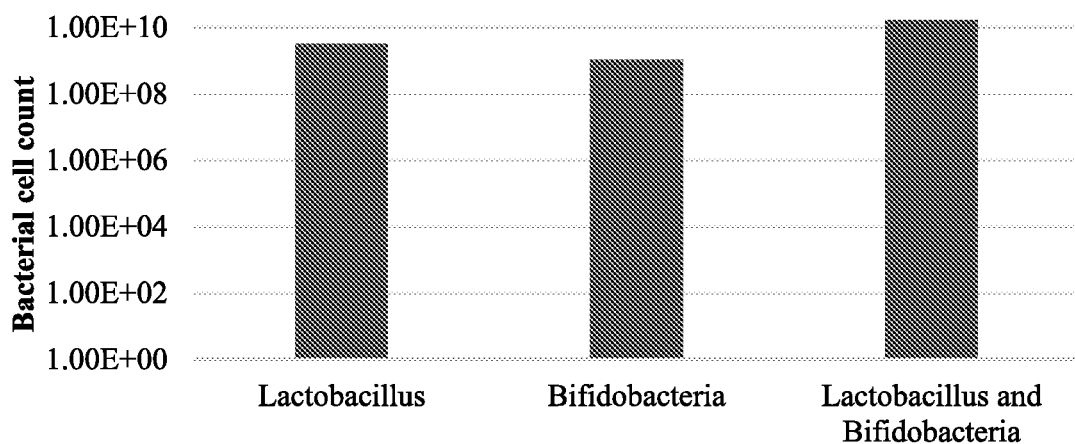
FIG. 7 is a bar graph showing the bacterial growth of *Lactobacillus* and *Bifidobacterium* strains and their mix in a medium scale.
Figure 8A:
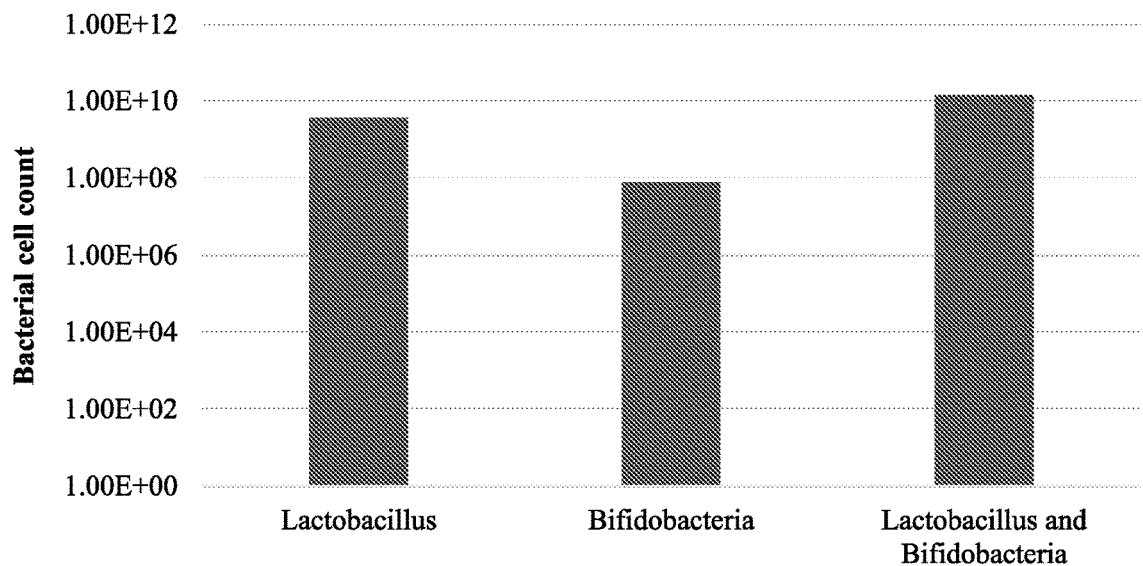
FIGS. 8A-8B are bar graphs showing the bacterial growth in accordance with different types of inoculum: bacterial detached from biofilm (FIG. 8A) or matrix inoculum (FIG. 8B).
Figure 8B:
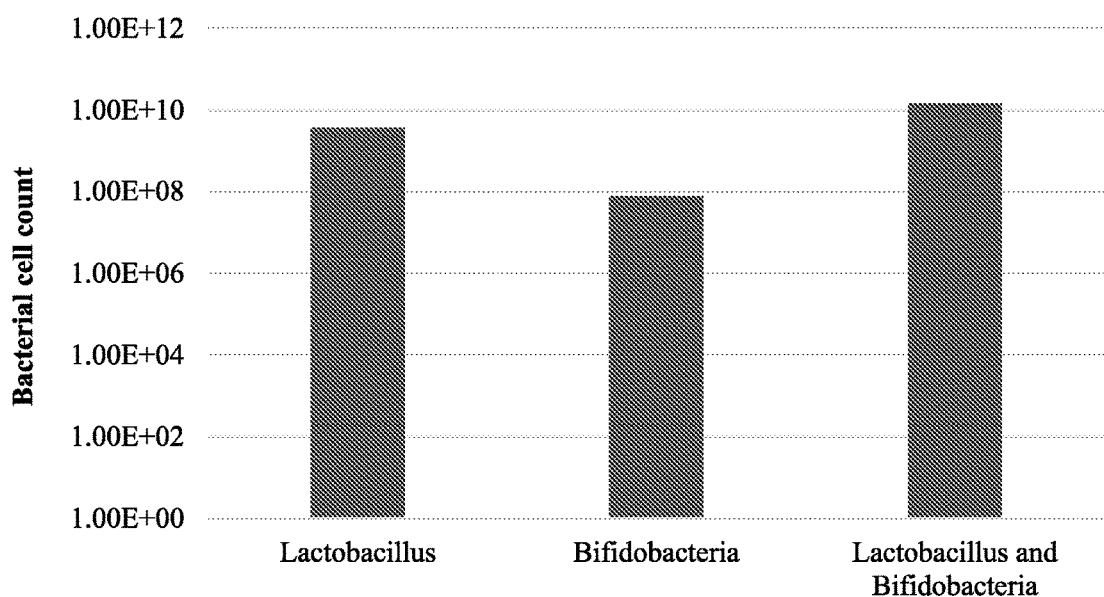

The bacterial growth of the soil and oral microbiota was observed in different media at each dilution performed in aerobic and anaerobic proliferative conditions. The bacterial growth observed in soil matrix and soil planktonic source was higher than the observed in the oral sample (in average more than 400 colonies/plate in soil samples vs 110 colonies in oral samples). With respect to migration in general, the results indicated good migration from small scale matrix to medium scale matrix. The amount of bacteria obtained after 24 hours of incubation at small scale are summarized in FIG. 6. After incubation, the inoculum from small scale matrix was transferred to medium scale matrix and the bacterial growth in average was improved, as illustrated in FIG. 7. Interestingly, a significant growth of bacteria was observed in the medium scale when Lactobacillus and Bifidobacterium were inoculated together. In addition, the bacterial migration was assessed according to two types of inoculation: bacteria that were detached from biofilm or biofilm matrix. The results, as demonstrated in FIG. 8, indicate that matrix inoculum may be advantageous for the Bifidobacterium growth.

Figure 9:
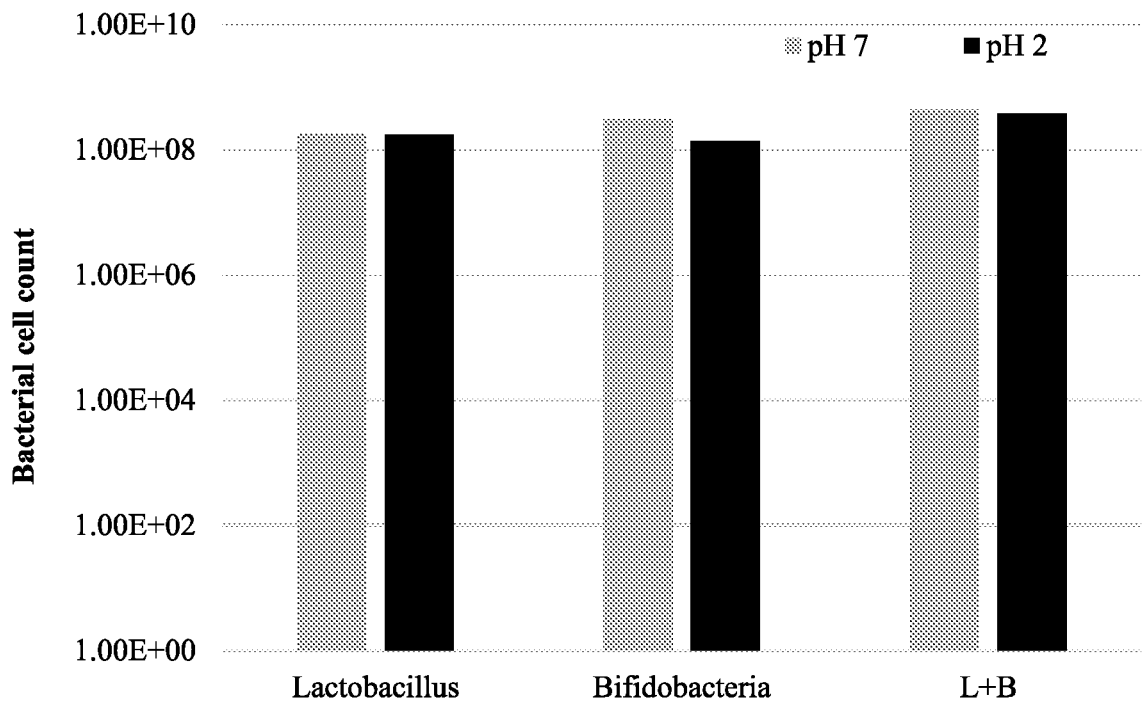
FIG. 9 is a bar graph showing the bacterial acid resistance by bacterial cell count in a medium scale conditions.

FIG. 9 indicated an acid resistance and bacterial survival at medium scale conditions. Thus, bacterial cell count is highly similar at pH 7 or pH 2. These results are in concordance with previous results and suggest a higher pH resistance of bacteria as a biofilm. No significant differences were observed in acid resistance test when the medium scale process started from a bacterial detached inoculum.

Example 5

L. plantarum strain was taken from a fresh plate and grown at 37° C. in 25 ml of MRS broth for 48 hours. 15 ml was transferred to the wheat bran tube and 7 ml to the pomegranate seeds tube and incubated for 3 days. Table 13 demonstrates the bacterial cell count per gram.

TABLE 13

|  | Wheat (plastic tube) | POM (plastic tube) |
| --- | --- | --- |
| Cell count (bacteria/gr) | $2.3*10^5$ | $7*10^6$ |

Example 6

Antibiotics Resistance

L. plantarum strain was grown at 37° C. in 200 ml of 25% MRS broth and 80 gr of DCP particles. The cap of the bottle had two silicone tubings that go all the way to the bottom of the bottle. One of the tubes from the bottle was connected to a 2 liter PVC bottle with a cap with two outings for silicone tubes. The PVC bottle was filled with 1500 ml of 25% MRS. The bottle was incubated in static conditions for 2 hours. Then, it was incubated in flow conditions on tilt shaker at 15 rpm for 6 days. Different concentrations of carbenicillin were added in order to test antibiotic resistance of: 0, 1, 2, 4, 8, 16, 32, 64, 128 and 256 µg/ml and were incubated overnight at 37° C. in static conditions.

Results

Figure 10:
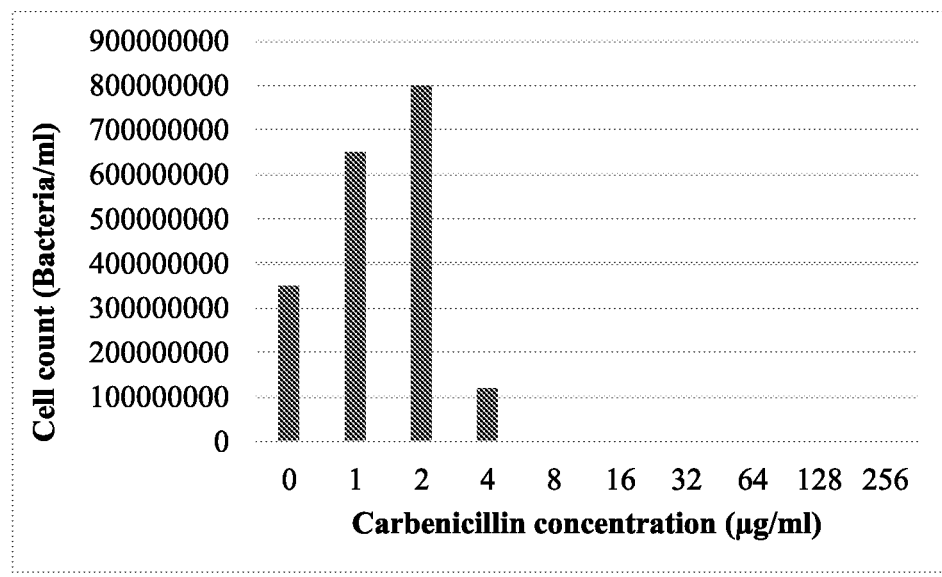
FIG. 10 is a bar graph showing bacterial strain resistance to antibiotics by bacterial cell count in varying concentrations of carbenicillin.

FIG. 10 illustrates the growth inhibition of L. plantarum strain from 4 µg/ml of carbenicillin.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A synthetic composition comprising a plurality of bacterial genera and a particle, wherein the plurality of bacterial genera is (i) a co-culture of at least two distinct bacterial families, comprising at least one bacterial subset of aerobic bacteria and at least one bacterial subset of anaerobic bacteria, and (ii) comprising at least 30% of bacterial families listed under any one of tables 9 and 11.

2. The composition of claim 1, comprising a bacterial co-culture of one or more bacteria selected from the group consisting of: Actinobacteria, Bacteroidetes, Deinococcus-Thermus, Firmicutes, Fusobacteria, Lentisphaerae, Proteobacteria, Synergistetes, Tenericutes, and Verrucomicrobia.

3. The composition of claim 1, comprising at least one bacterial subset of bacteria in the form of biofilm and at least one bacterial subset of planktonic bacteria.

4. The composition of claim 1, wherein said bacterial families constitute oral bacterial flora or a soil bacterial flora.

5. The composition of claim 1, wherein said plurality of bacterial genera is derived from an oral sample or a soil sample.

6. The composition of claim 1, wherein the said plurality of bacterial genera is derived from at least one origin.

7. The composition of claim 1, wherein the said plurality of bacterial genera is derived from one or more healthy mammal, animal donor, bacterial strain, stored microbiota sample, bacterial colony, planktonic sample and a biofilm.

8. The composition of claim 1, wherein said particle comprises a plurality of particles, and optionally further comprising a plurality of types of particles.

9. The composition of claim 8, wherein each particle comprises the co-culture of at least 2 distinct bacterial families.

10. A pharmaceutical composition comprising the composition of claim 1 and a pharmaceutically acceptable carrier or excipient.

11. The pharmaceutical composition of claim 10, wherein said pharmaceutically acceptable carrier or excipient is selected from one or more of a stabilizer, a preservative, a chelating agent, a viscosity modifying agent, a buffering agent, and pH adjusting agent.

12. The pharmaceutical composition according to claim 10, formulated for rectal, intravenous, parenteral, mucosal, nasal or oral administration.

13. A method of treating a disease or a disorder in a subject in need thereof, the method comprises administering to the subject the composition of claim 10.

14. The method of claim 13, wherein said disease or disorder is dysbiosis.

15. A method for obtaining the composition of claim 1, the method comprising the steps of:
a. providing a plurality of bacterial genera from at least one origin;
b. suspending said plurality of bacterial genera to receive a bacterial genera solution;
c. filtering the plurality of bacterial genera solution thereby obtaining a filtrate comprising the plurality of bacterial genera;
d. incubating the filtrate with a plurality of particles, and allowing the plurality of bacterial genera to attach to the plurality of particles;
e. dividing the plurality of bacterial genera attached to the plurality of particles, into a plurality of bacterial solution subsets;
f. culturing a first bacterial solution subset in a growth medium under aerobic conditions and a second bacterial solution under anaerobic conditions;
g. removing the growth medium, and recombining the first bacterial subset and the second bacterial subset;
thereby obtaining the composition comprising a co-culture of at least 2 distinct bacterial families, comprising at least one bacterial subset of aerobic bacteria and at least one bacterial subset of anaerobic bacteria, and comprising at least 30% of bacterial families listed under any one of tables 9 and 11.

* * * * *